(12) United States Patent
Subramaniam et al.

(10) Patent No.: US 10,745,335 B2
(45) Date of Patent: Aug. 18, 2020

(54) CONTINUOUS PROCESS FOR THE OZONOLYSIS OF LIGNIN TO YIELD AROMATIC MONOMERS

(71) Applicant: University of Kansas, Lawrence, KS (US)

(72) Inventors: Bala Subramaniam, Lawrence, KS (US); Andrew M. Danby, Lawrence, KS (US); Michael D. Lundin, Lawrence, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 16/317,173

(22) PCT Filed: Jul. 13, 2017

(86) PCT No.: PCT/US2017/041910
§ 371 (c)(1),
(2) Date: Jan. 11, 2019

(87) PCT Pub. No.: WO2018/013796
PCT Pub. Date: Jan. 18, 2018

(65) Prior Publication Data
US 2019/0248723 A1 Aug. 15, 2019

Related U.S. Application Data

(60) Provisional application No. 62/362,153, filed on Jul. 14, 2016.

(51) Int. Cl.
*C07C 45/40* (2006.01)
*C07G 1/00* (2011.01)
(Continued)

(52) U.S. Cl.
CPC .............. *C07C 45/40* (2013.01); *C07C 37/60* (2013.01); *C07C 37/70* (2013.01); *C07C 45/786* (2013.01); *C07G 1/00* (2013.01); *C08H 6/00* (2013.01)

(58) Field of Classification Search
CPC ......... C07C 45/40; C07C 37/60; C07C 37/70; C07G 1/00; C08H 6/00; C08H 8/00
See application file for complete search history.

(56) References Cited

U.S. PATENT DOCUMENTS

| | | |
|---|---|---|
| 5,074,960 A | 12/1991 | Nimz et al. |
| 5,385,641 A | 1/1995 | Berg et al. |

(Continued)

FOREIGN PATENT DOCUMENTS

WO  WO 2012/075053 A2  6/2012

OTHER PUBLICATIONS

Daphne Hermosilla et al., "The Application of Advanced Oxidation Technologies to the Treatment of Effluents from the Pulp and Paper Industry: A Review," 22 Environmental Science and Pollution Research 168 (2015).*

(Continued)

*Primary Examiner* — Nicholas E Hill
(74) *Attorney, Agent, or Firm* — Bell & Manning, LLC

(57) ABSTRACT

A method for processing lignin may comprise flowing a lignin composition comprising a lignin polymer and a solvent through a reaction chamber of a continuous flow reactor, the lignin polymer comprising hydroxycinnamic groups bound to a polymeric backbone; flowing ozone through the reaction chamber containing the lignin composition under conditions to maximize oxidative cleavage of the hydroxycinnamic groups to produce one or more types of aromatic monomers while minimizing oxidative cleavage of the polymeric backbone; and collecting the one or more (Continued)

types of aromatic monomers, e.g., by a size-selective membrane separation device.

20 Claims, 16 Drawing Sheets

(51) Int. Cl.
*C08H 7/00* (2011.01)
*C07C 37/60* (2006.01)
*C07C 37/70* (2006.01)
*C07C 45/78* (2006.01)

(56) References Cited

U.S. PATENT DOCUMENTS

| | | |
|---|---|---|
| 7,074,306 B2 | 7/2006 | Martelli et al. |
| 8,992,688 B2 | 3/2015 | Shevchenko et al. |
| 2004/0167019 A1 | 8/2004 | Liang et al. |
| 2010/0159521 A1 | 6/2010 | Cirakovic |
| 2010/0159522 A1 | 6/2010 | Cirakovic |
| 2012/0107886 A1 | 5/2012 | Albizati et al. |
| 2012/0187228 A1 | 7/2012 | Camp et al. |
| 2014/0034508 A1 | 2/2014 | Stecker et al. |
| 2014/0046099 A1 | 2/2014 | Stecker et al. |
| 2014/0234947 A1 | 8/2014 | Jones |
| 2015/0099868 A1 | 4/2015 | Yang et al. |
| 2015/0247009 A1 | 9/2015 | Mitchell |

OTHER PUBLICATIONS

Rodolfo Travaini et al., "Ozonolysis: An Advantageous Pretreatment for Lignocellulosic Biomass Revisited," 199 Bioresource Technology 2 (2016).*

The International Search Report & Written Opinion issued in International application No. PCT/US2017/41910 dated Sep. 28, 2017, pp. 1-6.

Quesada et al., "Chemical Characterization of Ozonated Lignin Solutions from Corn (*Zea mays*) Stalk and Poplar (*Populus deltoides*) Wood by Capillary Gas Chromatography," J. High Resol. Chromatogr., vol. 20, Oct. 1997, pp. 565-568.

Quesada et al., "Ozonation Products of Organosolvolytic Extracts from Vegetal Materials," J. Agric. Food Chem., vol. 46, No. 2, 1998, pp. 692-697.

Rodger M. Dorland, A Thesis: "The Ozonization and Structure of Lignin in Relation to Solubility in Bisulphite Solutions," McGill University, Apr. 1939, pp. 1-182.

\* cited by examiner

Hydroquinone 4-hydroxy-benzaldehyde

Vanillin

CONTINUOUS PROCESS FOR THE OZONOLYSIS OF LIGNIN TO YIELD AROMATIC MONOMERS

CROSS-REFERENCE TO RELATED APPLICATIONS

This application is a National Stage of International Application No. PCT/US2017/041910, filed Jul. 13, 2017, which claims the benefit of U.S. Patent Application No. 62/362,153, filed Jul. 14, 2016, the contents of each of which are herein incorporated by reference.

REFERENCE TO GOVERNMENT RIGHTS

This invention was made with government support under grant number 2011-10006-30362 awarded by the Department of Agriculture. The government has certain rights in the invention.

BACKGROUND

Lignin is an amorphous three-dimensional polymer consisting of phenylpropane structures. Lignin is formed from three monolignol monomers, p-coumaryl alcohol, coniferyl alcohol, and sinapyl alcohol, which undergo enzymatic polymerization resulting in a complex polymer linked via eleven types of covalent bonds. The β-O-4 linkage is the most common bond accounting for between 30% and 60% of all linkages.

Several oxidation techniques have been investigated for the production of aromatic monomers from lignin. Alkaline nitrobenzene oxidation (ANBO) has been used to determine the lignin polymeric structures via oxidative deconstruction to component monomers. Consequently, high yields of aromatic products have been reported. (Yamamura, M., Hattori, T., Suzuki, S., Shibata, D., Umezawa, T. *Plant Biotechnology* 27 305-310 (2010).) However, limitations on commercial utilization for monomer production include the requirement for stoichiometric quantities of nitrobenzene, high energy use and safety concerns due to possible explosions. There are also reports of catalytic wet oxidation methods being used to produce aromatic aldehydes utilizing expensive noble metal catalysts (Salesa, F. G., Maranhaob, L. C. A., Lima Filhob, N. M., Abreu, C. A. M. *Chemical Engineering Science* 62 5386-5391 (2007)), less expensive metals (Wu, G. X., Heitz, M. Journal of Wood Chemistry and Technology 15 189-202 (1995)) or Perovskite-type oxides (Zhang, Z., Deng, H., Lin, L. *Molecules* 14 2747-2757 (2009)). The main drawbacks to these methods are the expense of catalyst production, the cost and environmental concerns associated with the catalyst recovery and the use of large quantities of caustic reagents. The Borregaard plant in Norway uses a wet oxidation process to produce vanillin from lignosulphonates and, with the exception of vanilla bean extraction, it is currently the world's only supplier of vanillin derived from natural sources. Environmental remediation requirements of the wet oxidation process, along with the limited supply of lignosulphonates as the pulping industry has moved to alternative pulping processes, have limited its viability.

SUMMARY

Provided herein are methods for processing lignin, including for the production of aromatic monomers from the lignin.

In one embodiment, a method for processing lignin comprises flowing a lignin composition comprising a lignin polymer and a solvent through a reaction chamber of a continuous flow reactor, the lignin polymer extracted from herbaceous biomass and comprising hydroxycinnamic groups bound to a polymeric backbone; flowing ozone through the reaction chamber containing the lignin composition under conditions to maximize oxidative cleavage of the hydroxycinnamic groups to produce one or more types of aromatic monomers while minimizing oxidative cleavage of the polymeric backbone; and collecting the one or more types of aromatic monomers.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

FIG. 10A shows a spectrum of the lignin before ozonolysis; FIG. 10B shows a spectrum of ozonized lignin (contact time of 1 min.); and FIG. 10C shows a spectrum of ozonized lignin (contact time of 5 mins.). Reaction conditions: acetic acid (12 v/v % $H_2O$), T=70° C.

DETAILED DESCRIPTION

Provided herein are methods for processing lignin, including for the production of aromatic monomers from the lignin.

The present methods involve the use of ozone, a powerful oxidant produced in situ from oxygen via corona discharge. Ozone preferentially attacks olefinic bonds leading to the oxidative cleavage of C=C bonds. However, a challenge of using ozone is that it can also oxidize aromatic rings to yield aliphatic acids. Nevertheless, embodiments of the present methods limit such aromatic ring opening reactions to maintain the aromaticity of the resulting products. In addition, embodiments of the present methods are based on the inventors' understanding that certain groups (e.g., hydroxycinnamic groups) can be oxidatively cleaved by ozone while minimizing or preventing the oxidative cleavage of the polymeric backbone of the lignin, thereby maintaining the polymeric structure of the lignin during processing. This selective oxidation provides for a facile and clean recovery of only the desired aromatic monomers. The intact processed lignin may be further subjected to depolymerization processes, if desired. Unused ozone can be easily decomposed to oxygen, either thermally or using a catalytic bed, thereby minimizing any adverse environmental impact. Finally, by further contrast to conventional approaches to lignin oxidative depolymerization, the present methods employ readily available reactants, mild conditions, and benign solvents to produce high, controllable yields of aromatic monomer products with fast reaction times.

A method for processing lignin may first comprise flowing a lignin composition comprising a lignin polymer and a solvent through a reaction chamber (e.g., a reaction chamber of a continuous flow reactor). As further described below, in embodiments, the lignin polymer may be one which is extracted from herbaceous biomass and comprises hydroxycinnamic groups bound to a polymeric backbone. The method may further comprise flowing ozone through the reaction chamber containing the lignin composition. The method may be carried out under conditions to maximize oxidative cleavage of the hydroxycinnamic groups to produce one or more types of aromatic monomers while minimizing oxidative cleavage of the polymeric backbone. Finally, the method may further comprise collecting the one or more types of aromatic monomers.

Figure 1:
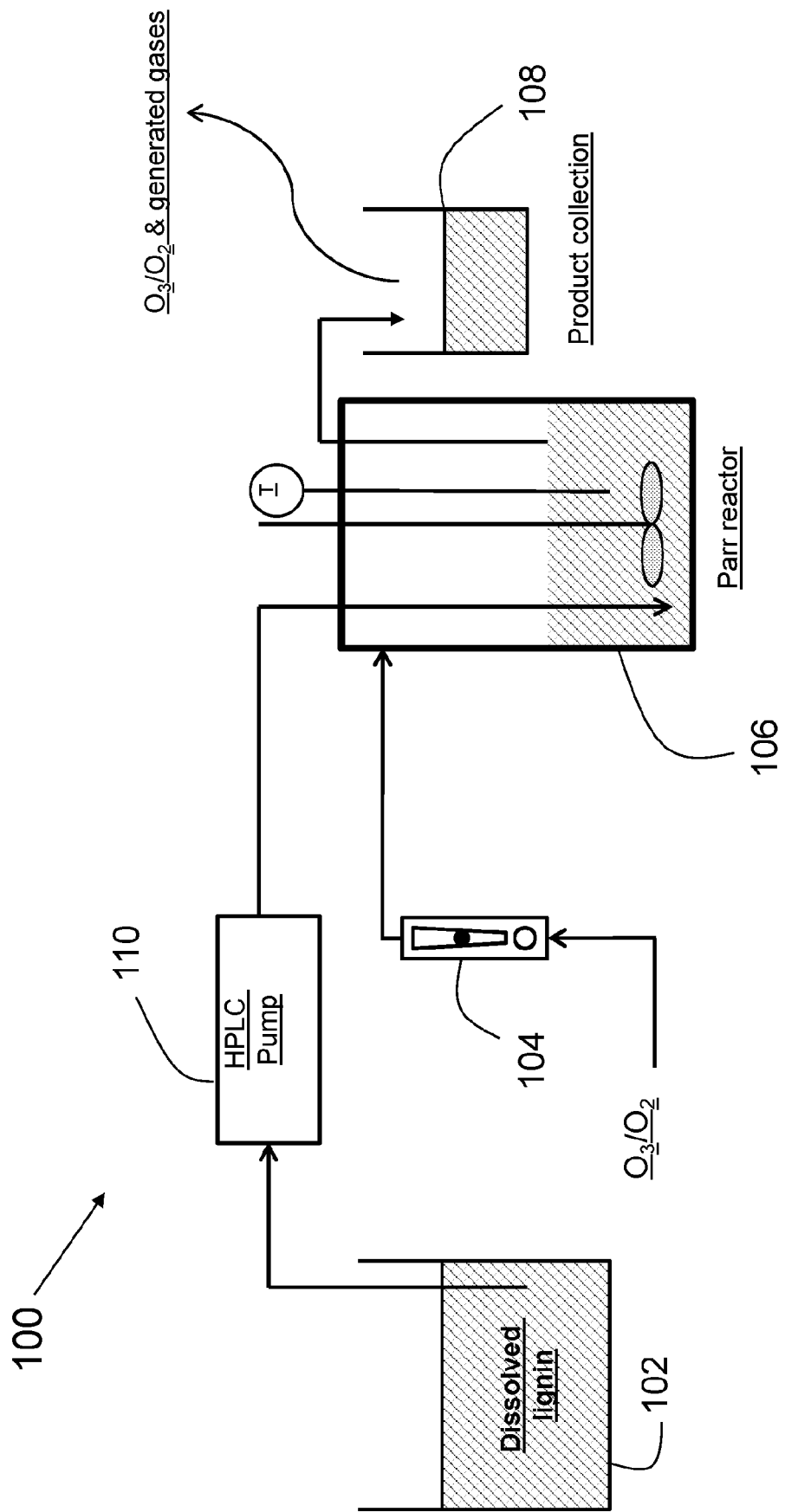
FIG. 1 is a schematic illustration of a portion of a continuous flow reactor system for lignin ozonolysis.

As noted above, the method may be carried out using a continuous flow reactor system. By "continuous flow reactor system" it is meant a system in which reactants and products are handled via a continuous, flowing stream. Continuous flow reactor systems are distinguished from batch reactor systems as well as semicontinuous reactor systems. An illustrative continuous flow reactor system 100 is shown in FIG. 1. The system 100 includes a first reactant source 102 (for the lignin composition), a second reactant source 104 (for the ozone), a reaction chamber 106 (in which oxidative cleavage of the lignin occurs), a collection chamber 108 (for the aromatic monomers), and a pump 110 configured to flow the lignin composition through the reaction chamber 106. Other components typically used in continuous flow reactor systems may be used.

Various configurations of the reactant sources 102, 104, the reaction chamber 106, and the product chamber 108 may be used, provided the configurations are appropriate for containing/generating the reactants, for achieving the oxidative cleavage reactions, and for containing unreacted lignin or byproducts/collecting aromatic monomers, respectively. The second reactant source 104 for ozone may provide ozone in a gas mixture, e.g., with oxygen. In the illustrative embodiment, the reaction chamber 106 is a stirred reaction chamber commercially available from Parr Instrument Company, which allows the lignin composition to be stirred in the reaction chamber during the oxidative cleavage reactions to promote and preferably maximize intimate mixing between the lignin component and ozone. It should be understood that such intimate mixing may be achieved using different means such as the use of ultrasound or spraying the lignin-laden solution as fine droplets into a gas stream containing ozone (for example, a spray reactor system is further described below). The reaction chamber 106 may be coupled to a heater (not shown) to achieve a selected reaction temperature. Reaction chambers having various volumes may be used, depending upon the selected volume of lignin composition and the selected reaction time. Various pumps may be used depending upon the selected flow rate and the need to handle the lignin.

By "conditions," as that term is used with respect to the method, can refer to the flow rate of the lignin composition (which affects the reaction time), the flow rate of ozone-containing stream, the volume of the reaction chamber (which also affects the reaction time), the reaction temperature, the stirring rate, etc. These conditions may be adjusted to achieve a desired yield for a particular aromatic monomer and/or a desired total yield of aromatic monomers while preserving a majority of the lignin backbone. The flow rate of the lignin composition and the volume of the reaction chamber occupied by the lignin composition (referred to as the holdup volume) determine the reaction time between the lignin composition and the ozone. The holdup volume is typically smaller than the total volume of the reaction chamber. Thus, this flow rate and holdup volume may be selected depending upon the desired reaction time. Illustrative reaction times include those in the range of from about 0.1 minutes to about 40 minutes, from about 0.5 minutes to about 20 minutes, or from about 1 minute to about 10 minutes. Illustrative flow rates of the gas stream containing 3-10 mole % ozone include those in the range of from about 50 std dm$^3$/hr to about 100 std dm$^3$/hr, with sufficient ozone being preferably available to cleave all the pendant aromatic groups (i.e., hydroxycinnamic groups). Illustrative reaction temperatures include those less than about 150° C. or less than about 100° C. This includes embodiments in which the reaction temperature is in the range of from about 20° C. to about 100° C., from about 20° C. to about 80° C., from about 30° C. to about 90° C., or from about 40° C. to about 80° C. Illustrative stirring rates include those in the range of from about 200 rpm to about 1700 rpm, from about 400 rpm to about 1000 rpm, or from about 500 rpm to about 750 rpm. Mixing may also be accomplished by bubbling the ozone-containing gas through the liquid in the reaction chamber.

Another type of continuous flow reactor which may be used to carry out the present methods is a spray reactor. In a spray reactor, the lignin composition may be sprayed as fine droplets into an ozone-containing gas stream to enhance interfacial area (between the lignin composition and the ozone) as well as to control the contact time (reaction time) between the two phases. An illustrative spray reactor which may be used is described in M. Li, et al., "A Spray Reactor Concept for Catalytic Oxidation of p-Xylene to Produce High-purity Terephthalic Acid," *Chemical Engineering Science.* 104, 93-102 (2013), which is hereby incorporated by reference in its entirety. The spray reactor includes a chamber having a certain diameter and length which is configured to spray the lignin composition from the top of the chamber as a fine shower of droplets. The spray shower is met by a flowing stream of ozone-laden gas. By controlling the contact time between the ozone and the droplets, certain groups on the polymeric backbone of lignin may be oxidatively cleaved while minimizing the oxidative cleavage of the polymeric backbone itself. The ozonized stream is collected at the bottom of the spray reactor as a liquid. The contact time between the ozone-laden gas stream and the droplets may be controlled in a number of ways. In one configuration, the length of the spray tower may be shortened thereby limiting exposure of the products to the countercurrently flowing ozone stream. In another configuration, the ozone-laden gas stream may be flowed at a relatively fast rate across the droplets in a cross-current fashion (rather than in counter- or co-current fashion) to achieve the same results; viz., minimizing the contact time between ozone and the droplets.

Unlike batch reactors or semicontinuous reactors, continuous flow reactors such as those shown in FIG. 1 or based on a spray reactor allow for precise control of the ozone contact with the lignin composition. This facilitates maximizing the oxidative cleavage of aromatic molecular groups from the lignin polymer while minimizing over-oxidation of the cleaved products and oxidation of the remaining polymeric backbone of the lignin. For fast reactions (e.g., less than 10 minutes or less than 5 minutes), it is not possible to precisely control the reaction time using batch or semicontinuous reactors.

Figure 8B:
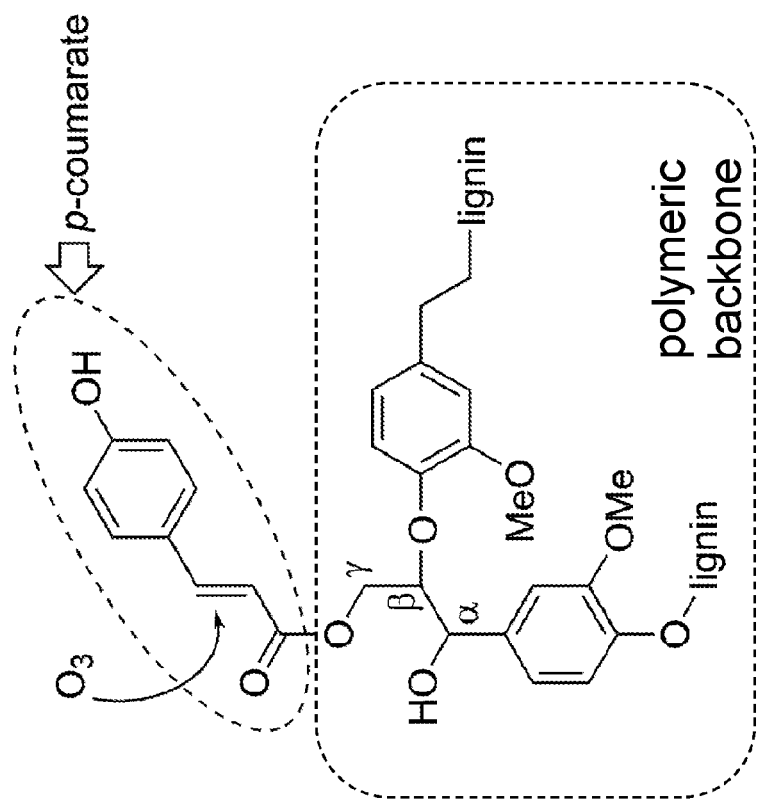
FIG. 8B shows the chemical structure of a typical grass lignin having a p-coumarate ester (i.e., a hydroxycinnamic group) at Cγ.

The lignin composition includes lignin and a solvent. The lignin may be characterized by the natural source from which the lignin is extracted as well as the procedure used to extract the lignin. A variety of natural sources of biomass may be used to generate lignin. The biomass may include agricultural waste, agricultural product, forestry waste or forestry product. The biomass may include herbaceous plants, plants that have no persistent wood stem above ground. Specific, illustrative types of herbaceous biomass include corn stover and wheat straw. The inventors have determined that lignin from herbaceous plants is particularly susceptible to ozone mediated oxidative cleavage reactions. As shown in FIG. 8B, herbaceous lignin is composed of p-coumarate groups (i.e., hydroxycinnamic groups) covalently bound to a polymeric backbone at $C\gamma$, with an olefinic bond between the $\alpha$ and $\beta$ carbons in the coumarate. The amount of p-coumarate groups depends upon the type of herbaceous lignin. By way of illustration, maize lignin contains from about 7% to about 12% by weight of p-coumarate groups ("by weight" refers to the weight of the p-coumarate groups as compared to the weight of the dry lignin). Other types of lignin, including non-herbaceous lignin, may be used, although such lignin may have smaller amounts of p-coumarate groups. The inventors have found that the olefinic bond attaching the p-coumarate groups to the polymeric backbone of the lignin is highly susceptible to ozone attack. The inventors have further found that the conditions of the present methods may be selected to maximize oxidative cleavage of these olefinic bonds while minimizing/preventing over-oxidation of the cleaved aromatic products as well as minimizing/preventing oxidative cleavage of the polymeric backbone of the lignin. This allows for a cleaner and more facile recovery of only desired aromatic products as compared to conventional lignin oxidative depolymerization schemes (which result in a large number of products requiring extensive separation techniques for isolation (which is often incomplete)).

Lignin may be extracted from biomass using several techniques, including organosolv, steam explosion, dilute acid hydrolysis, alkali extraction and wet oxidation procedures. Organosolv procedures refer to the use of an aqueous organic solvent, optionally in combination with mineral acid, at temperatures ranging from ca. 70 to 220° C. to extract the lignin from the natural source. The particular procedure may be selected to maximize the yield of lignin. In this disclosure, lignin extracted via organosolv procedures may be referred to as "organosolv lignin." A variety of organosolv procedures may be used. Two illustrative organosolv procedures, an ethyl acetate protocol and a methyl isobutyl ketone (MIBK) procedure, which differ primarily by solvent composition and extraction time, are described in the Example, below.

After extraction, the lignin, or a portion thereof, is dissolved using a solvent. A variety of solvents may be used, provided the solvent is able to dissolve at least a portion of the lignin. While a majority of the lignin is expected to be dissolved in the solvent, this is not a requirement. In other words, some of the lignin may also be simply suspended in the liquid being pumped (i.e., the lignin composition). In embodiments, the solvent is a short chain carboxylic acid. In some embodiments, the short chain carboxylic acid is combined with water. The number of carbon atoms in the short chain carboxylic acid may be in the range of from about 1 to 6, from about 1 to 5, or from about 1 to 3. Illustrative short chain carboxylic acids include formic acid, acetic acid, and propionic acid. The particular solvent and the relative amount of short chain carboxylic acid and water may be selected to achieve a desired yield for a particular aromatic monomer and/or a desired total yield of aromatic monomers while preserving a majority of the lignin backbone. Illustrative amounts of water include those in the range of from about 2% to about 25% by volume, from about 5% to about 20% by volume, or from about 5% to about 15% by volume (the balance being made up by the short chain carboxylic acid). In some embodiments, only the short chain carboxylic acid is used as the solvent such that the lignin composition is substantially free (i.e., free, but not necessarily perfectly free) of any other components beside the lignin and the short chain carboxylic acid. In some embodiments, only the short chain carboxylic acid and water are used as the solvent such that the lignin composition is substantially free (i.e., free, but not necessarily perfectly free) of any other components beside the lignin, the short chain carboxylic acid, and the water. Various amounts of the lignin may be used in the composition. The particular amount depends on the solubility of the lignin used at the selected reaction temperature. Illustrative amounts include from about 0.1% by weight to the amount at saturation concentration. "By weight" refers to the weight of the lignin obtained as compared to the total weight of the lignin composition. "Saturation concentration" is the concentration of lignin above which concentration any additional lignin added does not dissolve in the selected solvent.

Figure 7:
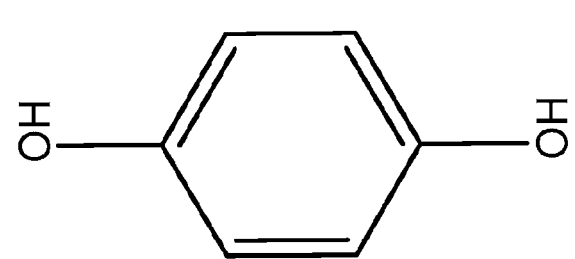
FIG. 7 shows the chemical structures of three products, vanillin, 4-hydroxybenzaldehyde and hydroquinone.
Figure 7:
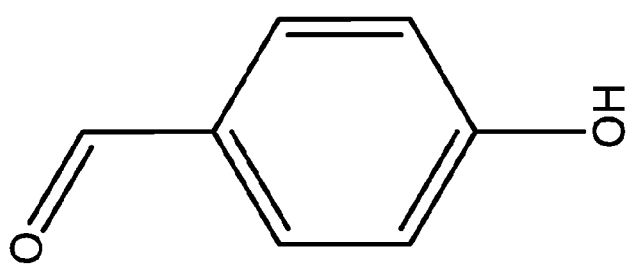
Figure 7:
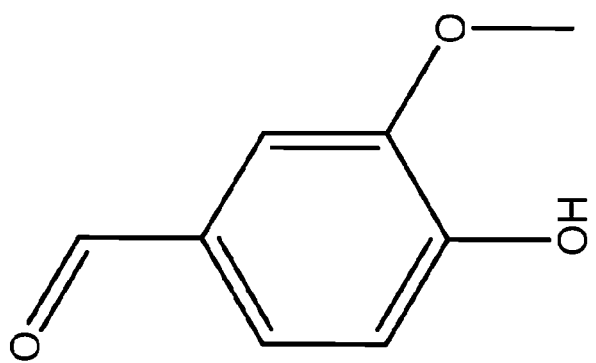

As further described in the Example below, the present methods are able to achieve high yields of aromatic monomers. Moreover, the yield of a particular aromatic monomer can be tuned by adjusting the conditions used during the method (as well as the solvent for the lignin composition). The aromatic monomers can include vanillin, 4-hydroxybenzaldehyde, and hydroquinone. The chemical structures of these monomers are shown in FIG. 7. Other aromatic monomers include, but are not limited to, vanillic acid and 4-hydroxybenzoic acid. In embodiments, the method yields vanillin and 4-hydroxybenzaldehyde, i.e., substantially only these two aromatic monomers. In embodiments, the method yields vanillin, vanillic acid, 4-hydroxybenzaldehyde, and 4-hydroxybenzoic acid, i.e., substantially only these four aromatic monomers. By "substantially only" it is meant that the method yields the polymeric backbone of the lignin, the named aromatic monomers, and less than 5% by weight, less than 2% by weight, less than 1% by weight, or less than 0.1% by weight of unidentified product. The "unidentified product" may be a collection of trace amounts of other aromatic monomers and/or small molecules. "By weight" refers to the weight obtained as compared to the weight of the original dry lignin (not the lignin composition) used in the method. In such embodiments, the method may be characterized as providing one or more types of aromatic monomers selected from vanillin, 4-hydroxybenzaldehyde, vanillic acid, 4-hydroxybenzoic acid, and combinations thereof. The phrase "selected from" is used to indicate that no other aromatic monomers are produced other than combinations of the named aromatic monomers or that other unnamed aromatic monomers are only present in trace amounts.

Yields include those of at least 0.1% by weight, at least 0.3% by weight, at least 0.5% by weight, at least 1% by weight, at least 2% by weight, at least 3% by weight, at least 4% by weight, at least 5% by weight, at least 6% by weight, at least 10% by weight, or at least 15% by weight. "By weight" refers to the weight of the aromatic monomers obtained as compared to the weight of the original dry lignin (not the lignin composition) used in the method. This includes embodiments in which the yield is in the range of from about 0.1% by weight to about 15% by weight. These yields may refer to an individual aromatic monomer or the total yield of all the aromatic monomers.

As noted above, embodiments of the present methods are capable of maximizing the oxidative cleavage of the olefinic bonds attaching hydroxycinnamic groups to the polymeric backbone of the lignin while also minimizing/preventing over-oxidation of the cleaved aromatic products. In embodiments, the total yield of the cleaved aromatic products is substantially the same as the amount of hydroxycinnamic groups in the unprocessed lignin. By "substantially the same" it is meant that the total yield and the amount of hydroxycinnamic groups in the unprocessed lignin are within, e.g., +10%, ±5%, ±2%, or less of each other.

Yields may be determined by Gas-Chromatography with Flame Ionization Detector (GC-FID) as described in the Examples, below.

At the same time, as noted above, embodiments of the present methods are able to minimize/prevent oxidative cleavage of olefinic bonds within the polymeric backbone of the lignin. In embodiments, the conditions of the method results in substantially no oxidative cleavage of the polymeric backbone of the lignin. The lack of oxidative cleavage may be confirmed by using gel permeation chromatography as described in the Examples, below. By "substantially no oxidative cleavage" it is meant that the average molecular weight (as measured using gel permeation chromatography) of the processed lignin is not more than 20%, not more than 15%, not more than 10%, or not more than 5% lower than the average molecular weight (as measured using gel permeation chromatography) of the unprocessed lignin. Two-dimensional (2D) NMR may be additional used to confirm lack of oxidative cleavage, i.e., 2D-NMR spectra of the processed lignin and unprocessed lignin will be essentially the same.

Since embodiments of the present methods can provide processed lignin having a substantially intact polymeric backbone, the methods may further comprise subjecting the processed lignin to one or more additional depolymerization processes. The type of depolymerization process is not limited. Prior to applying these depolymerization processes, the processed lignin may be separated from the one or more types of aromatic monomers, e.g., by using size-selective membrane filtration (e.g., nanofiltration as described in Example 3, below). Size-selective membrane filtration may be used to retain more than 90%, more than 95%, or more of the processed lignin while selectively rejecting the one or more types of aromatic monomers. Nanofiltration may be also used as a way of collecting the aromatic monomers as also described in Example 3.

It is noted that the lignin compositions used in the methods are also encompassed by the disclosure.

EXAMPLES

Example 1

Materials and Methods
Organosolv Lignin Extraction from Corn Stover:
Lignins from three sources were investigated as substrates for the reaction. Two were derived from post-harvest corn stover waste grown in Douglas County, Kans. The corn stover was chopped into small pieces (<2 mm diameter) using a blender before being dried in a vacuum oven at 40° C. for 16 hours. Lignin was then extracted from the corn stover using one of the following organosolv extraction processes (i) MIBK process—10 g of corn stover and 1 ml concentrated $H_2SO_4$ were added to 100 ml of a solution containing methyl isobutyl ketone (MIBK):ethanol:water (20:35:45 v/v %). The mixture was placed in a stirred stainless steel autoclave, heated to 140° C. and stirred for 120 minutes. After cooling, the solution was filtered and then water was added to the solution to cause phase separation. The organic phase was separated from the aqueous phase and the lignin was isolated from the organic phase by evaporation of the solvent. (ii) EtOAc process—the procedure was as described for the MIBK process except that the solvent mixture was ethyl acetate:ethanol:water (36.7:25.0: 38.3 v/v %) and the mixture was heated to 140° C. and stirred for only 20 minutes. The third lignin substrate was provided by the Archer Daniels Midland (ADM) Company.

Size Exclusion Chromatography:
The molecular weight distributions of the isolated lignins were determined using Gel Permeation Chromatography (GPC) performed on an Agilent 1260 Infiniti GPC system fitted with an Agilent refractive index detector. Two columns were used in series at 40° C., a 300 mm Polargel-M followed by a 300 mm Polargel-L, and the samples eluted with DMF at a flow rate of 1.0 ml $min^{-3}$. Poly(methyl methacrylate) standards were used for calibration.

GC Mass Spectrometry:
The starting material (i.e., lignin) and recovered product solution were analyzed by GC-MS and GC-FID by diluting 2 µL of recovered product with 1 mL of hexane. The GC method uses an HP-INNOWAX column on an Agilent 7890A GC coupled to a 5975C MS and uses a carrier gas flow of 1 std $cm^3$ $min^{-1}$, an inlet temperature of 250° C., and an injection volume of 1 µL; the oven temperature was initially held at 40° C. for 5 min, then ramped at 10° C. per minute to 220° C. and held at this temperature for a further 20 min. Masses were scanned from 20 to 500 Da.

GC FID:

Product analysis was performed using GC/FID. 300 μL of the product mixture was added to 1 ml of methanol or ethyl acetate and the sample run on an Agilent 7890A GC with a 30 m HP-INNOWAX column and FID detector using the same method as used for the GC MS analysis described above. Products were identified by comparison of retention times with known standards and quantified using relative response factors with mesitylene as internal standard.

Results and Discussion

Figure 6:
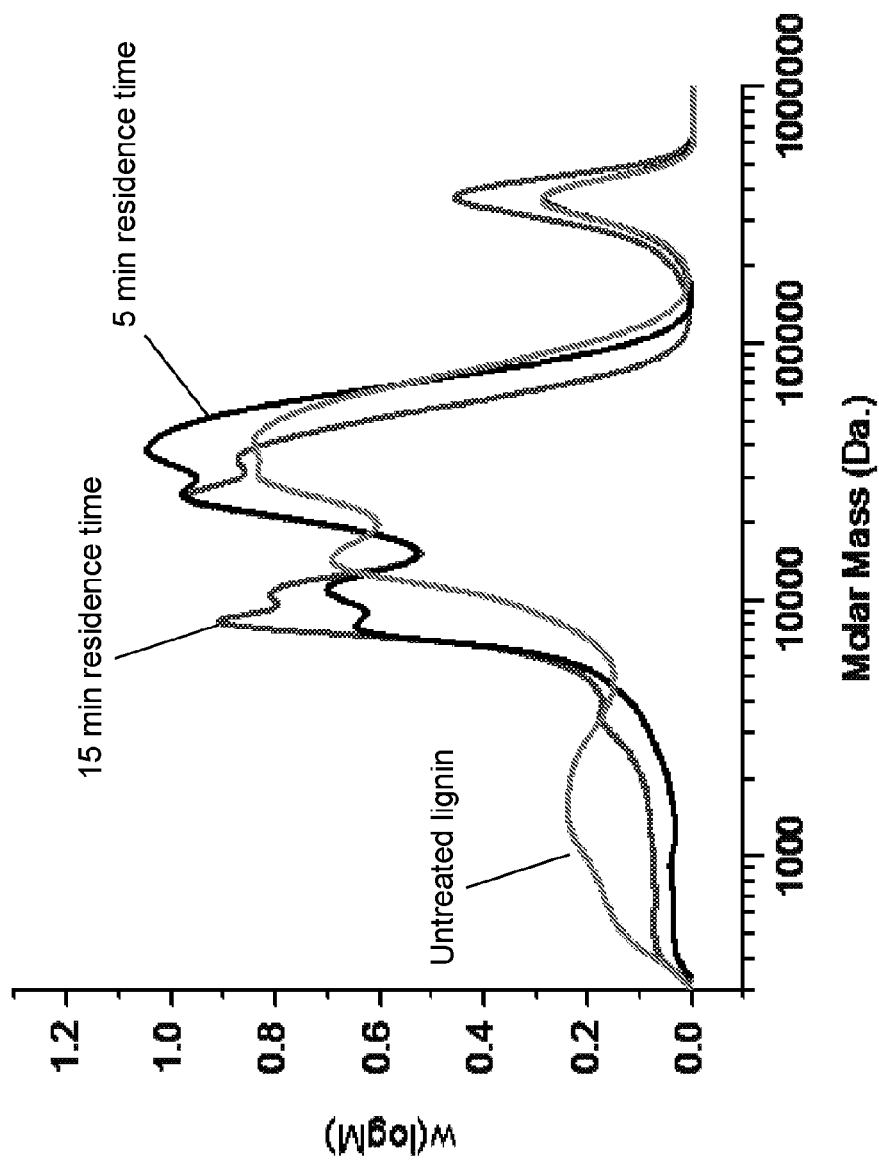
FIG. 6 shows the gel permeation chromatogram of the products of the continuous ozonolysis of MIBK lignin in formic acid at 70° C.

Lignin Isolation:

As described above, two similar organosolv methods were used to isolate lignin from corn stover. One utilized a solvent mixture comprising of ethyl acetate, ethanol and water, whereas the other used methyl isobutyl ketone (MIBK), ethanol and water. Both used sulphuric acid at between 0.05 mol dm$^{-3}$ and 0.12 mol dm$^{-3}$ as a catalyst. The ethyl acetate method consistently gave lignin yields of ca. 10 wt % whereas the MIBK method gave lignin yields of ca. 9 wt % Efforts to maximize lignin yields were not made since the primary loss of lignin was thought to be during the aqueous/organic phase separation step and repeated washing of the aqueous phase appeared to introduce impurities into the lignin. The lignin as isolated had a broad range of molecular weights as measured by size exclusion chromatography (SEC), with three notable maxima at 41 kDa, 32 kDa and 14.2 kDa relative to poly(methyl methacrylate) standards (FIG. 6).

Continuous Ozonolysis System:

It was observed from performing ozonolysis of lignin in a batch reactor that yields of aromatic products decreased with increasing reaction time. Shortening the reaction times in the batch reactor gave irreproducible results. Because the desired ozonolyis reaction of cleaving only the pendant groups occurs rapidly (on the order of a few minutes), precise control of the reaction time in a batch reactor was not possible. Hence, a reactor suitable for continuous ozonolysis of a lignin solution was designed and built, in which the contact time between the lignin and ozone is controllable with significantly better precision than in a batch reactor. The continuous system was based upon a stirred Parr reactor and is shown schematically in FIG. 1. The lignin, dissolved in a suitable solvent (ca. 1 wt %) and filtered through a 0.45 μm filter, was pumped into the heated and stirred reactor (stirring at 750 rpm) using an HPLC pump at flow rates between 0.71 and 10 ml min$^{-1}$. An ozone/oxygen gas mixture was fed into the top of the reactor at a flow rate of 70 std dm$^3$ hr$^{-1}$. Level control was via a dip tube with a multiphase exit flow. It was found that the HPLC pump had inadequate flow rate for short residence times and it was replaced with an ISCO 500D syringe pump in later experiments. The measured volume of liquid in the cell was 14.2 ml. In a typical experiment, air is fed into the reactor headspace with a flow rate between 50 and 100 dm$^3$/hr and the reactor temperature is adjusted to between 30° C. and 70° C. After establishing steady liquid and gas flow rates at desired values, and upon reaching the predetermined reactor temperature, the ozone generator was switched on under the conditions described above. All reaction products were collected as they were purged from the reactor by the gas stream with a collection interval of 0.5× residence time (defined as the liquid holdup (here, 14.2 mL) in the reactor divided by the volumetric liquid flow rate). Excess ozone was purged from the collected liquid sample by bubbling nitrogen gas through the sample for 10 seconds.

Continuous Ozonolysis of Lignin in Formic and Acetic Acids:

Continuous lignin ozonolysis reactions were performed to examine the effect of several variables including, (i) lignin source, (ii) residence time, (iii) solvent, specifically formic acid vs. acetic acid and water content of acetic acid, and (iv) temperature. Products were quantified using GC techniques as described above. As shown in Table 1, in all experiments, the two major products were 4-hydroxybenzaldehyde and vanillin. Hydroquinone was also observed in many experiments. In all experiments there were approximately 20 other products many of which were identified by GC/MS to be aromatic compounds. Among these products included vanillic acid and 4-hydroxy-benzoic acid. Rough quantification by GC/FID suggests their summed yield to be similar, but slightly less than the sum of the three quantified products (4-hydroxybenzaldehyde, vanillin, hydroquinone).

Figure 2A:
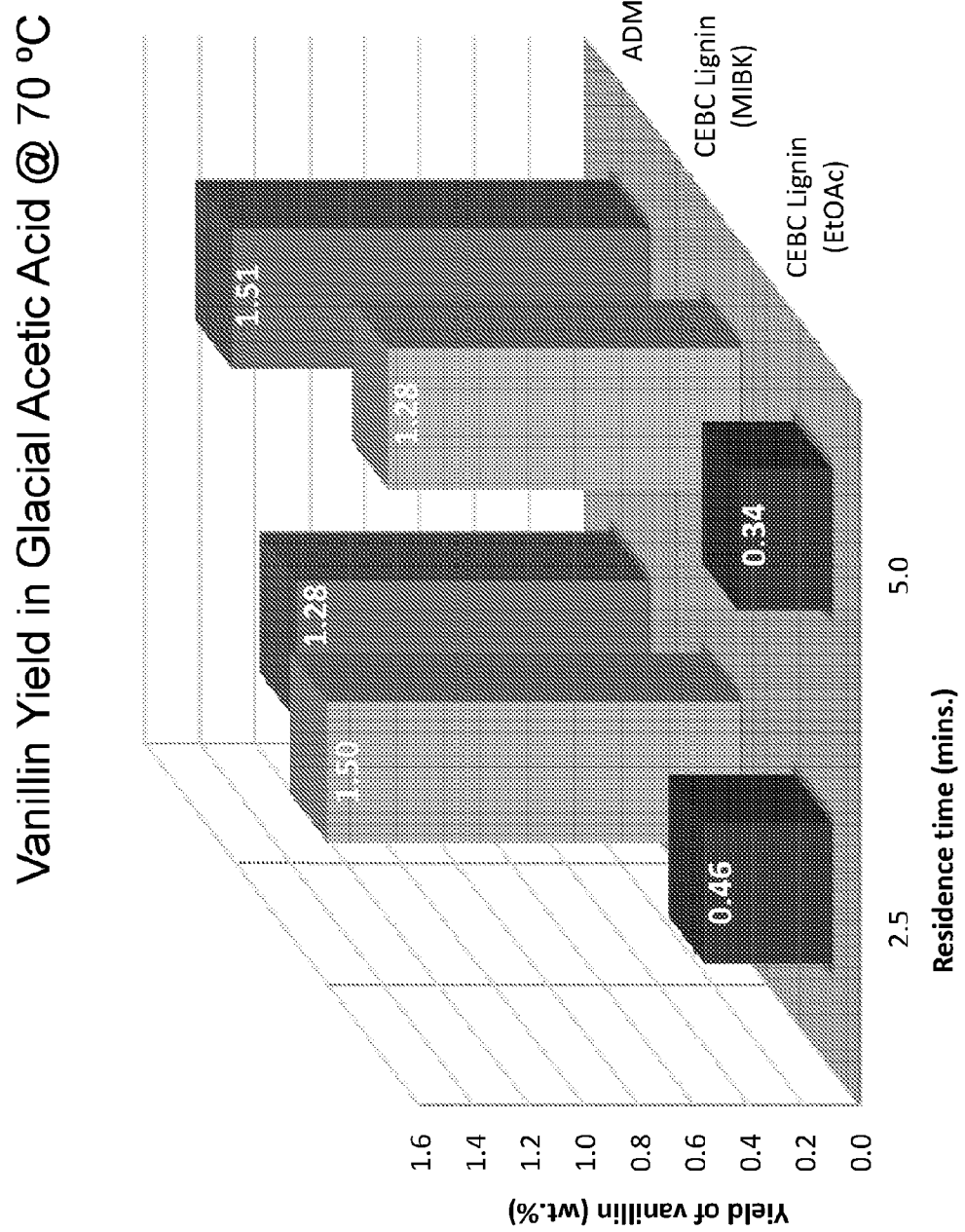
FIG. 2A shows the yield of vanillin as a function of the lignin source.
Figure 2B:
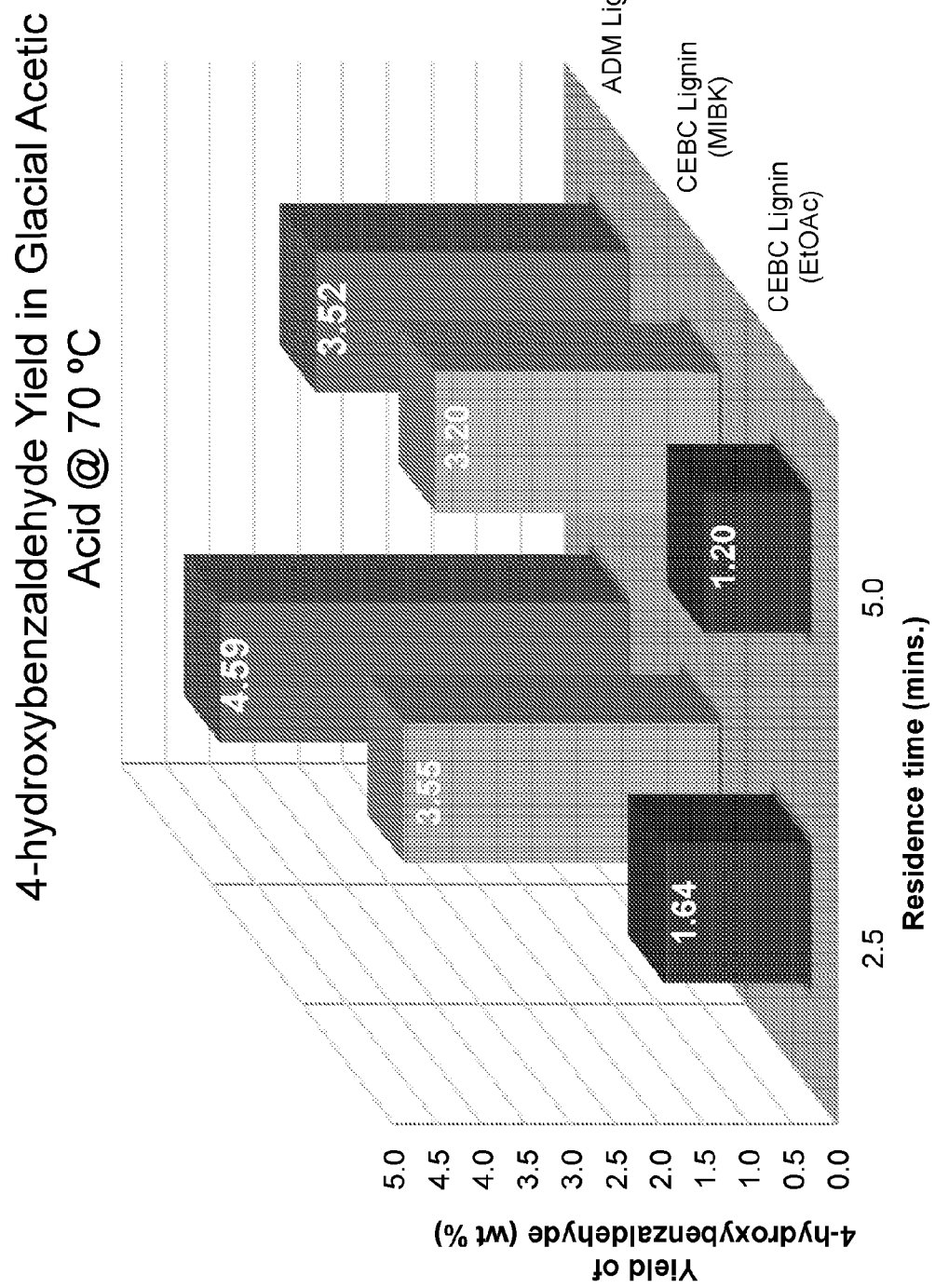
FIG. 2B shows the yield of 4-hydroxybenzaldehyde as a function of the lignin source.

Lignin Source:

Three sources of lignin were initially used for comparison; the two organosolv lignins extracted as described above and a lignin derived from corn stover and supplied by ADM. As shown in FIGS. 2A and 2B, the lignin extracted with the ethyl acetate protocol gave significantly lower product yields compared to the lignin extracted with the MIBK protocol and that supplied by ADM. The ADM lignin and the MIBK lignin give similar yields. A possible explanation of the difference between the EtOAc and MIBK lignins is the H$_2$SO$_4$ concentration used in the extraction method. H$_2$SO$_4$ is a dehydration catalyst and it is possible that at higher concentrations in the MIBK extraction it is dehydrating the lignin yielding a lignin richer in olefinic content.

Figure 3:
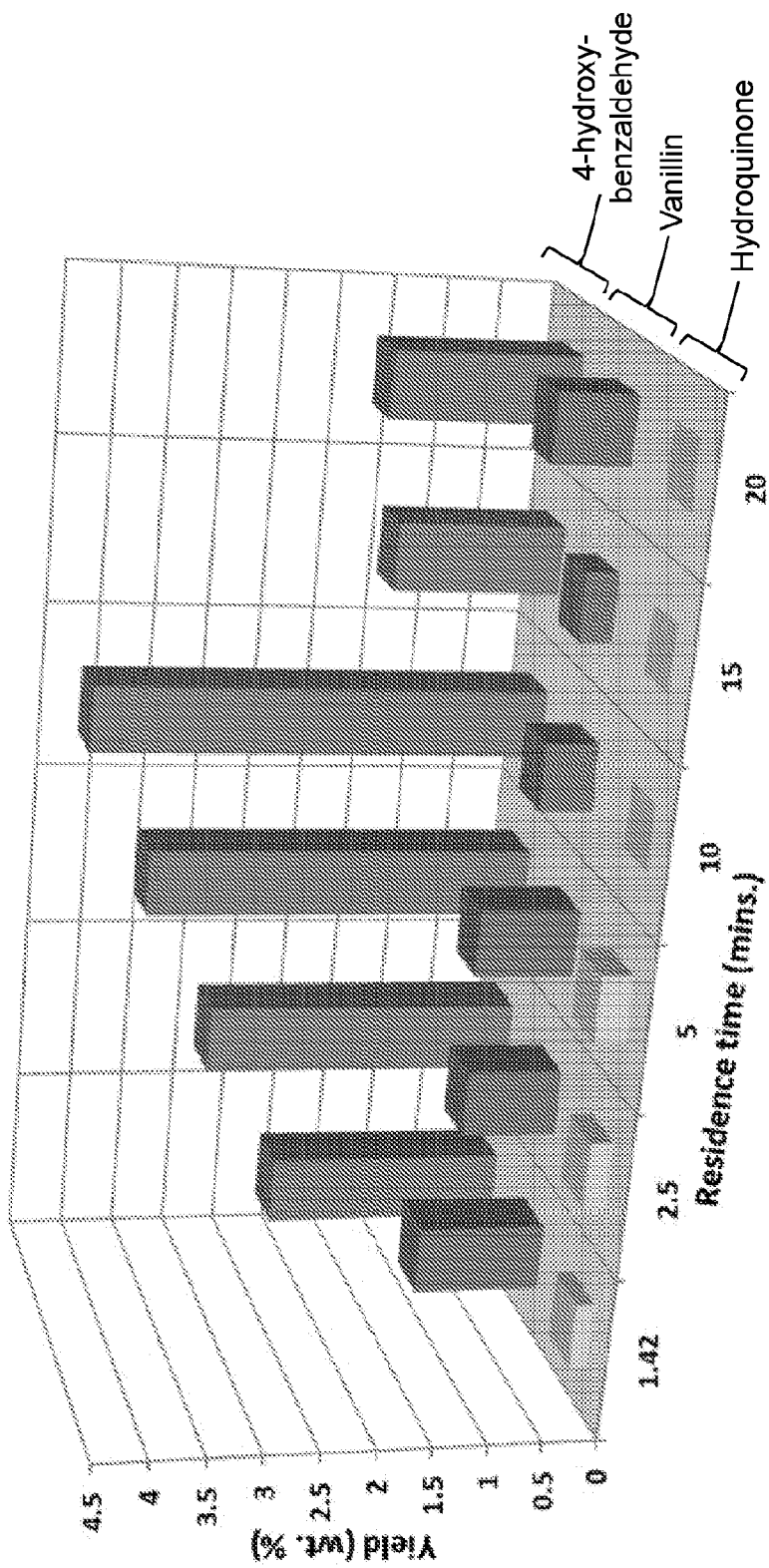
FIG. 3 shows the product yield as a function of residence time.

Residence Time:

Two patterns were observed when studying the effect of residence time on product yield. As shown in FIG. 3, the yields of vanillin were higher with shorter residence time whereas the yields of 4-hydroxy-benzaldehyde and hydroquinone reached maxima at certain residence times before decreasing at longer residence times. Studies of the ozonolysis of vanillin in formic acid showed no conversion to 4-hydroxybenzaldehyde, but vanillic acid was observed.

Figure 4:
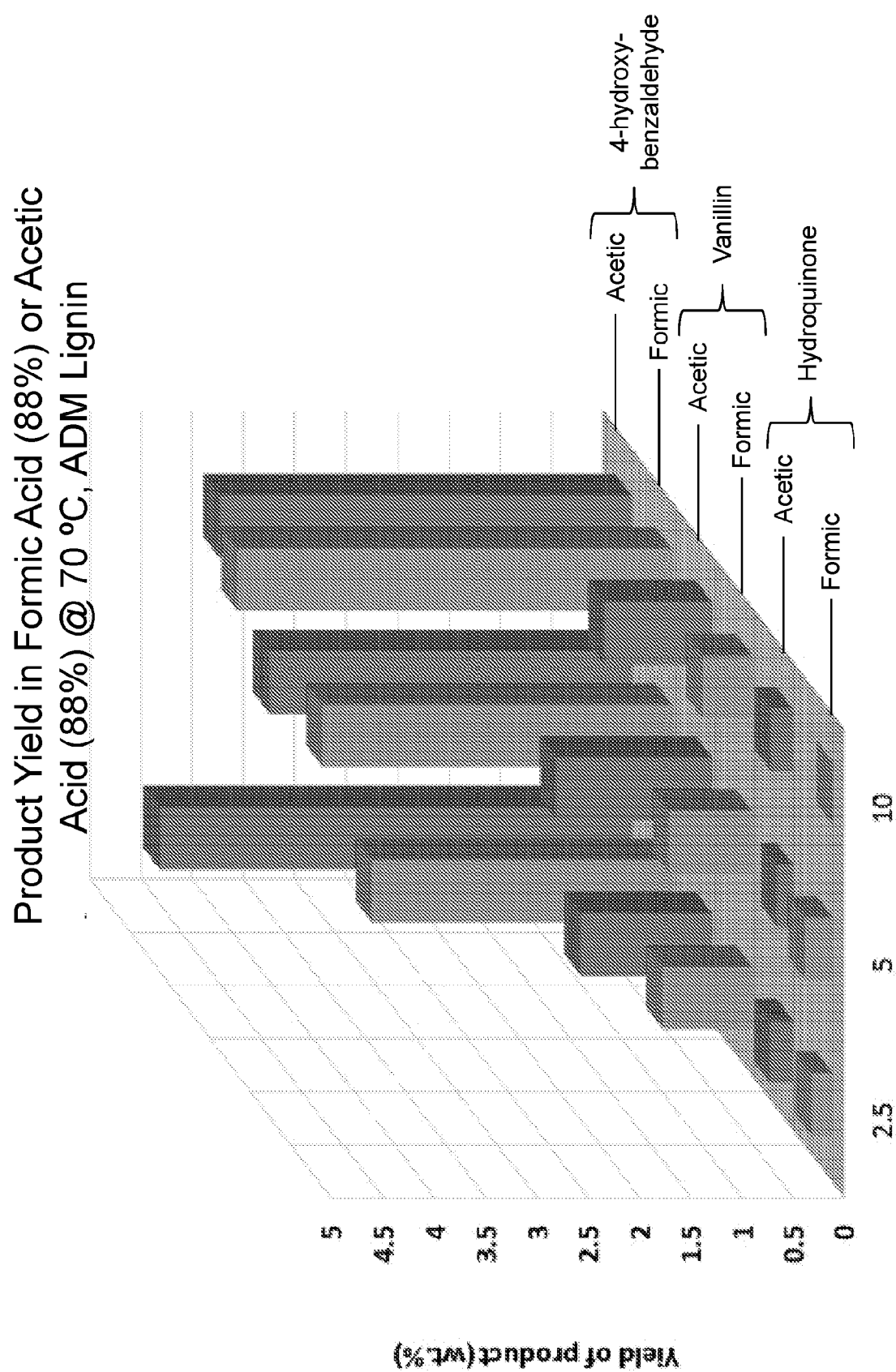
FIG. 4 shows the product yield as a function of residence time and solvent type.
Figure 5A:
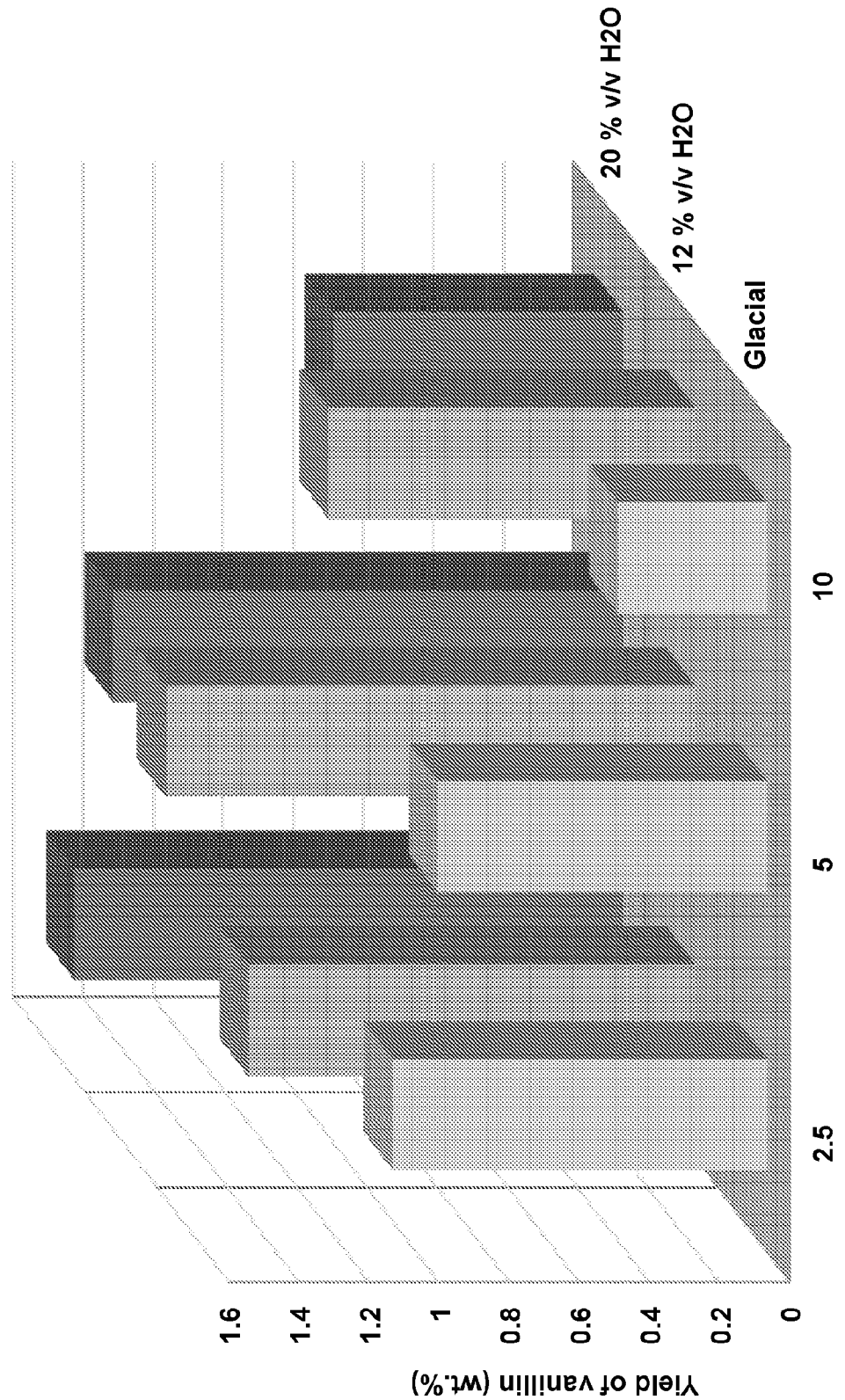
FIG. 5A shows the yield of vanillin as a function of residence time and water content in acetic acid.
Figure 5B:
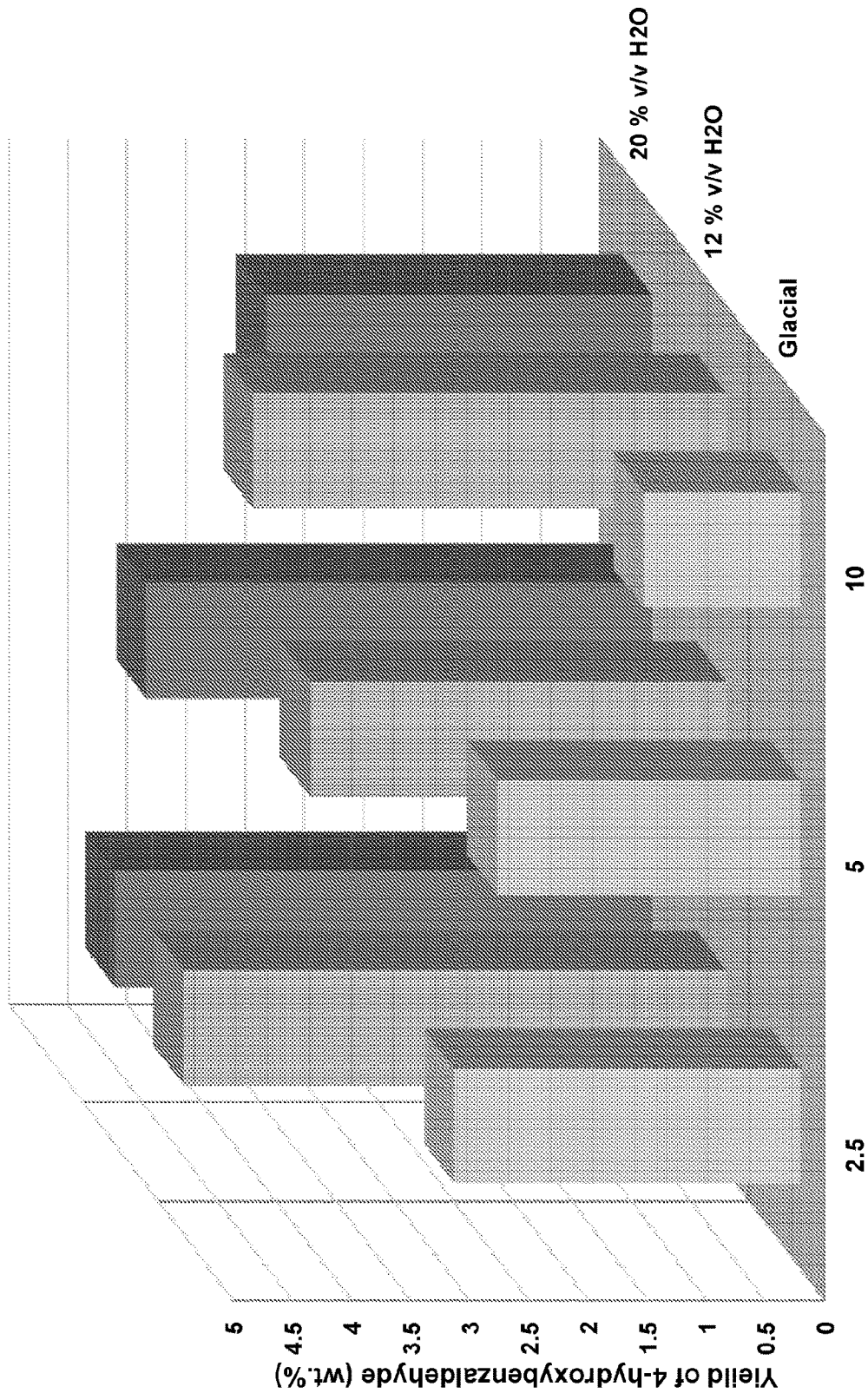
FIG. 5B shows the yield of 4-hydroxybenzaldehyde as a function of residence time and water content in acetic acid.
Figure 5C:
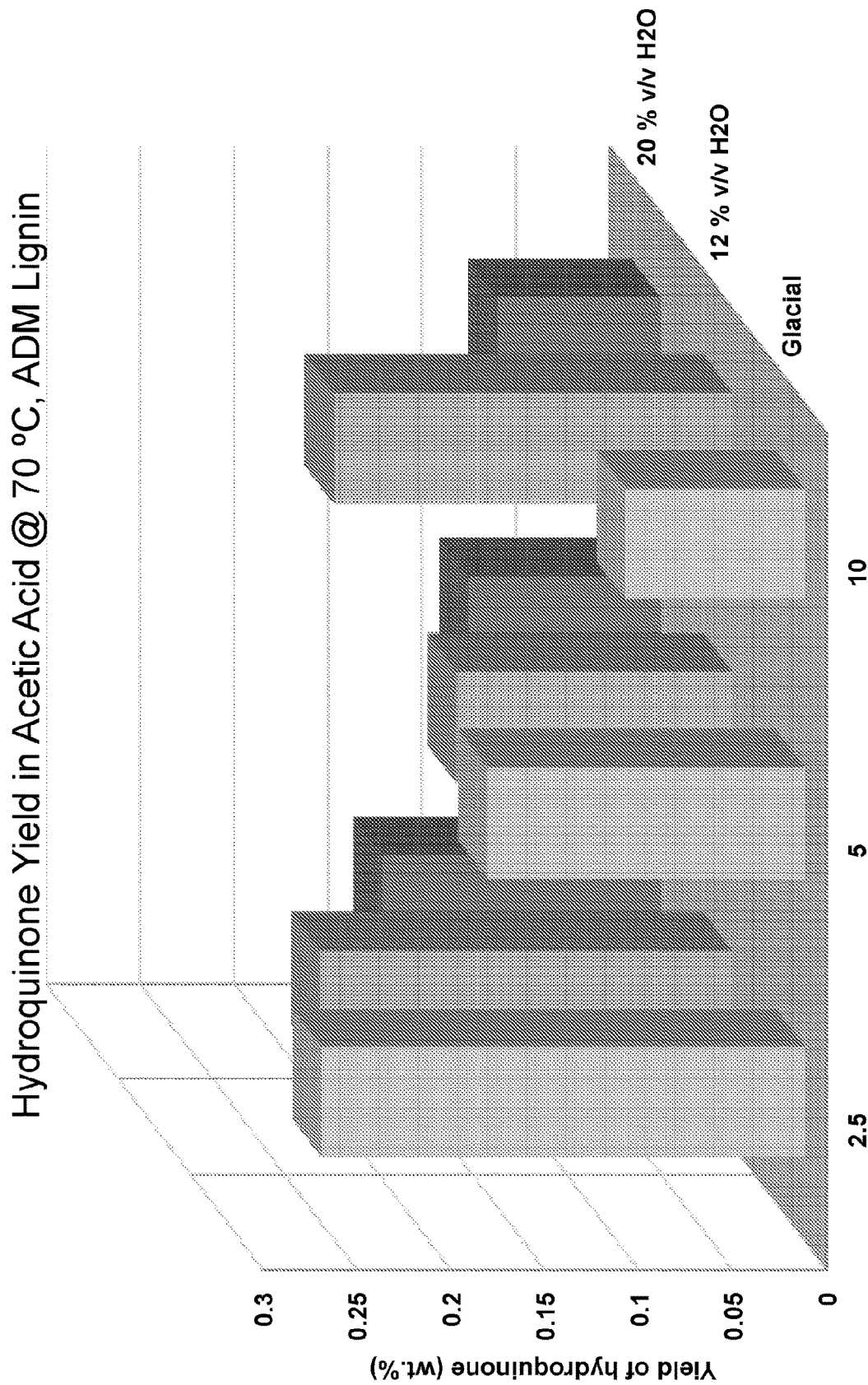
FIG. 5C shows the yield of hydroquinone as a function of residence time and water content in acetic acid.

Solvent:

As shown in FIG. 4, lignin ozonolysis in formic acid was found to give lower yields of aromatic products than when performed under identical conditions in acetic acid. Subsequent reactions were then performed in acetic acid. A study of the effect of water concentration in acetic acid on product yields demonstrated that water present at a concentration of 12 v/v % and above increased the yield of vanillin (FIG. 5A) and 4-hydroxy-benzaldehyde (FIG. 5B) compared to the yield in glacial solvent. However, greater yields of hydroquinone were found in glacial solvent up to water present at a concentration of 12 v/v % (FIG. 5C). Water concentrations above 20 v/v % could not be studied due to the limited solubility of lignin under those conditions.

Temperature:

Reducing the temperature from 70° C. to 30° C. had little effect on the yield of vanillin, increased the yield of hydroquinone and reduced the yield of 4-hydroxybenzaldehyde.

After ozonolysis, a large quantity of "unreacted" lignin remained dissolved in the solvent. After solvent removal, SEC of the residue revealed that there had been partial depolymerization of the lignin polymer. As shown in FIG. 6, it appeared that the molecular weight of the polymer molecules had shifted to specific lower molecular weights. This may indicate that rather than a random depolymerization, in which it would be expected for the heavier molecules to depolymerize into fragments of varying molecular weight from monomer to unreacted lignin, rather the lignin is undergoing particular bond breaking to yield polymers of a narrow range of molecular weights beyond which depolymerization via ozonolysis is not possible.

TABLE 1

Yields of monomeric products from the continuous ozonolysis of organosolv lignins in formic acid, acetic acid and the acids mixed with quantities of water.

| Lignin source | Temp. (° C.) | Solvent Acid (H$_2$O %) v/v | Residence time (mins) | Yield (wt %) vanillin | 4-hydroxy-benzaldehyde | hydroquinone |
|---|---|---|---|---|---|---|
| CEBC MIBK | 70 | Glacial Acetic | 2.5 | 1.50 | 3.55 | 0.30 |
|  |  |  | 5.0 | 1.28 | 3.20 | 0.22 |
| CEBC EtOAc | 70 | Glacial Acetic | 2.5 | 0.46 | 1.64 | 0.29 |
|  |  |  | 5.0 | 0.34 | 1.20 | n/a |
| ADM | 70 | Glacial Acetic | 2.5 | 1.07 | 2.93 | 0.26 |
|  |  |  | 5.9 | 0.94 | 2.57 | 0.17 |
|  |  | Acetic (12%) | 2.5 | 1.28 | 4.59 | 0.22 |
|  |  |  | 5.0 | 1.51 | 3.52 | 0.14 |
|  |  |  | 10.0 | 1.05 | 4.00 | 0.21 |
|  |  | Acetic (20%) | 2.5 | 1.46 | 4.28 | 0.10 |
|  |  |  | 5.0 | 1.56 | 4.54 | 0.15 |
|  |  |  | 10.0 | 0.83 | 3.26 | 0.09 |
| ADM | 70 | Formic (12%) | 1.42 | 1.17 | 2.20 | 0.16 |
|  |  |  | 2.5 | 0.87 | 2.92 | 0.21 |
|  |  |  | 5.0 | 0.91 | 3.60 | 0.29 |
|  |  |  | 10.0 | 0.48 | 4.22 | n/a |
|  |  |  | 15.0 | 0.29 | 1.55 | n/a |
|  |  |  | 20.0 | 0.71 | 1.74 | n/a |
| ADM | 30 | Formic (12%) | 5.0 | 0.83 | 3.05 | 0.55 |
|  |  |  | 10 | 0.81 | 3.12 | 0.44 |

Example 2

Introduction

The lack of a simple process for valorizing the lignin produced during cellulosic ethanol manufacture is a major hurdle preventing such biorefineries from becoming economically sustainable. Grasses and woody plants form lignin by the oxidative polymerization of hydroxycinnamyl alcohol monomers which vary in the degree of ring methoxylation. (2) This leads to a variety of bonds between the monomers that make lignin hard to degrade (3)—a trait that is good for the plant but one which makes it difficult to deconstruct lignin to recover valuable aromatics, since even if a depolymerization technique that is universally applicable to all types of inter unit bonds is used, the result is a complex mixture of products. (4, 5)

This example further demonstrates a facile ozonolysis process for selectively isolating a high value, high purity product stream by cleaving C=C bonds associated with specific pendant groups (hydroxycinnamic acid groups). These pendant groups are present in relatively high amounts in corn stover and wheat straw lignins. Without this ozonolysis process, it is not possible to harvest these pendant groups cleanly since depolymerization of the entire lignin typically produces myriad compounds that are difficult and expensive to separate. The resulting products, vanillin and 4-hydroxybenzaldehyde, constitute approximately 7 wt % of the lignin and command high value with established applications in the flavoring, pharmaceutical and electronics industries. Further, they are easily separated unlike typical product mixtures from lignin depolymerization that contain myriad compounds and require extensive downstream processing. Additionally, the remaining lignin following ozonolysis retains its polymeric structure and is available for further utilization. The recovered monomer products are conservatively estimated to generate 1.75-2.83 U.S. $ per gallon of ethanol produced, a range that favors a sustainable biorefinery.

Figure 8A:
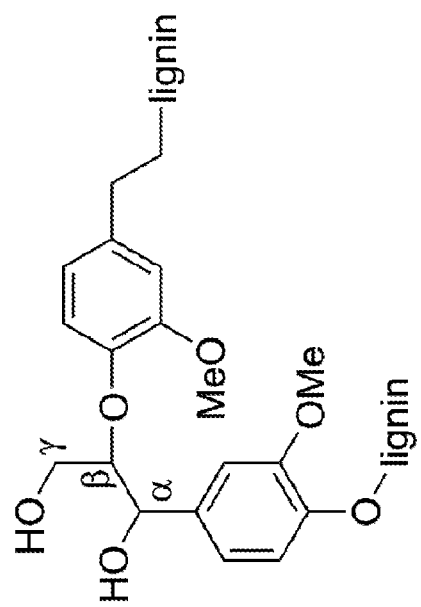
FIG. 8A shows the chemical structure of a typical woody lignin in which the lignin is hydroxylated at Cγ.

Many naturally occurring lignins are partially acylated via incorporation of pre-acylated monolignols in the Cγ position during the polymerization process. (14) Several studies have shown that various types of acids may be added to the monolignols, (15-17) depending upon the plant species. For example, acetates are observed in low abundance in hardwoods and at high levels in abaca, kenaf, palms and sisal. (14) (See FIG. 8A.) In contrast, p-hydroxybenzoates are found in palms and Populus species such as aspen, poplar and willow, while p-coumarates are abundant in grasses with maize (Zea mays L.) having the highest abundance of all common species. (6) (See FIG. 8B.) The acylation has been shown to occur predominantly on syringyl units, with 7-10% of p-coumarates reported on guaiacyl units. (18, 19) The ozonolysis process used in this example (as well as that of Example 1), is based, at least in part, on the inventors' understanding that ozone should readily attack the olefinic bond between the α and β carbons in the p-coumaric acid of the acylated lignin to yield 4-hydroxybenzaldehyde and/or 4-hydroxybenzoic acid upon cleavage and further, that the process could be optimized to selectively attack such olefinic bonds.

Materials and Methods

Lignins from three sources were used in the studies. Corn (Zea mays L.) stover derived lignin was provided by Archer Daniels Midland Company (Decatur, Ill.). Two lignins were extracted in the laboratory using the techniques described below. All solvents and reagents were supplied by either Fisher Scientific (Pittsburgh, Pa., USA) or Sigma-Aldrich (St. Louis, Mo., USA) and were used as supplied. Oxygen, Extra Dry 99.6% was supplied by Matheson.

Lignin Isolation

From wheat straw: Air-dried wheat straw (Everest) grown in Wyandote County, Kans. was milled such that the ground particles passed through a 1.7 mm sieve. This material was dried at 50° C. for 24 hours in a vacuum oven. Prior to the extraction step, the wheat straw was washed in batches with hexane by stirring a mixture of wheat straw (4 g) with hexane (100 mL) in a conical flask at room temperature for 5 minutes. The wheat straw was filtered and washed with a further 50 ml hexane. After further air drying overnight an ethyl acetate/ethanol/water-based organosolv extraction was performed. (29) A solution comprising ethyl acetate, ethanol, water and concentrated sulphuric acid was prepared in a 36.5/24.9/38.1/0.5 w/w % ratio. This solution (110 mL) was added to wheat straw (10.0 g) in a 300 mL Autoclave Engineers' high pressure reactor (316 stainless steel). The reactor was sealed, flushed with inert gas (3×15 psi N$_2$). The slurry was then stirred at 300 rpm and heated to 140° C., holding at that temperature for approximately 20 minutes. The reactor contents were then cooled to room temperature and the undissolved fraction was filtered and washed with 2×15 ml of the original solution minus the H$_2$SO$_4$. Water was added to the resulting liquor to cause phase separation. The two resulting phases were then separated in a separating funnel. Lignin (0.9 g) was isolated from the organic phase by removing the solvent in a rotary evaporator.

From hardwood: Kiln-dried American White Oak shavings (ca. 6 mm×10 mm×1 mm) were used for lignin extraction. Prior to organosolv extraction, 10 g of the shavings were placed in a 300 mL Autoclave Engineers' high pressure reaction vessel along with 200 mL of water. The vessel was sealed, flushed with inert gas and then heated to 160° C. for 10 minutes. After cooling to room temperature, the wood was isolated by filtration and air dried. A lignin isolation procedure identical to that employed for wheat straw utilizing ethyl acetate, ethanol, water and concentrated sulphuric acid in a 19/13/18/1 ratio was used with the pre-treated white oak shavings. After cooling the mixture was filtered and 200 ml of water was added to the resultant liquor. Ethyl acetate (ca. 60 ml) was added sufficient to effect phase separation. The organic phase was collected and combined with the washings of the aqueous phase (2×40 ml of ethyl acetate). The solvent was then removed from the organic phase in a rotary evaporator to yield 1.21 g of lignin.

Continuous Ozonolysis

The continuous ozonolysis of lignin was performed in a stirred Parr reactor having a set-up similar to that shown in FIG. 1. The conditions used for the continuous ozonolysis were also similar to those described above in Example 1. Briefly, the lignin, dissolved in the solvent at a concentration of ca. 1 wt % was filtered through a 0.45 μm filter. It was then pumped into the heated and stirred reactor (500 rpm) using either an HPLC pump or Teledyne-ISCO 500D syringe pump at a flow rate between 0.71 to 14.20 mL min$^{-1}$. An ozone/oxygen gas mixture containing ~3.5 mol % $O_3$, generated using a Praxair-Trailigaz Uniozone LO ozone generator from extra dry oxygen (Matheson), was fed into the top of the reactor at a flow rate of 70 std L hr$^{-1}$. The liquid level in the reactor was determined by the extent to which a dip tube is inserted into the reactor. The liquid and the gas exited the reactor via the dip tube in a multiphase flow. The measured volume of liquid in the reactor was 14.2 mL. Contact time is defined as the liquid holdup in the reactor divided by the volumetric liquid flow rate. In a typical experiment, a steady reactor temperature was achieved first after establishing the liquid and gas flow rates at desired values. Following this step, the ozone generator was switched on to introduce ozone in the gas stream. The reactor contents were collected as they were purged from the reactor by the gas stream with a collection interval of 0.5× contact time. Excess ozone was purged from the collected liquid samples by bubbling nitrogen gas through the sample for 10 seconds. Analysis revealed that a steady state was always achieved within three contact times.

Size Exclusion Chromatography

The molecular weight distributions of the isolated lignins were determined using Gel Permeation Chromatography (GPC) performed on an Agilent 1260 Infiniti GPC system fitted with an Agilent refractive index detector. Two columns, a 300 mm Polargel-M followed by a 300 mm Polargel-L, were used in series at 40° C. The samples were eluted with DMF (with 0.1 wt % tetrabutyl-ammonium bromide) at a flow rate of 1.0 ml min$^{-1}$. Poly(methyl methacrylate) standards were used for calibration.

Gas Chromatography

The starting material and recovered product solutions were analyzed with GC-MS and GC-FID by diluting between 50 and 300 μL of recovered product solution with 1 mL of hexane. 2,5-dimethoxytoluene was used as internal standard for the GC analysis. The GC method used an HP-INNOWAX column on an Agilent 7890A GC coupled to a 5975C MS and uses a carrier gas (He) flow of 1 std cm$^3$ min$^{-1}$, an inlet temperature of 250° C., and an injection volume of 1 μL. The oven temperature was initially held at 40° C. for 5 min, then ramped at 10° C. per minute to 220° C. and held at this temperature for a further 20 min. Masses were scanned from 20 to 500 Da. Some samples were silylated using and excess of N,O-bis(trimethylsilyl)trifluoroacetamide and pyridine. Products were identified by comparison of retention times with known compounds and from their mass spectrometry fragmentation patterns. Quantification was performed using GC-FID and calibration curves prepared from known samples.

HPLC

HPLC analysis was performed using a Varian ProStar HPLC system fitted with a dual channel UV detector (210 nm and 254 nm). The analyses were performed isocratically with a mobile phase (0.5 mL min$^{-1}$) consisting of water/acetonitrile/acetic acid in an 89/10/1 v/v ratio and an Aminex HPX-87H (300×7.8 mm) column at 25° C. Compounds were identified by comparing retention times with those for reference compounds.

NMR Spectroscopy

NMR spectra were recorded using a Bruker AVUI 500 MHz spectrometer. Approximately 100 mg of lignin or ozonized lignin product was dissolved in 0.7 mL dimethylsulfoxide-d6. Cr(acac)$_3$, at a concentration of 0.002 M, was used as a relaxation agent. For the $^{13}$C NMR analysis, an inverse-gated decoupling sequence was used to screen out the Nuclear Overhauser Effect (NOE) with the following parameters: 308 pulse angle, 2 s relaxation delay, 64 K data points, and 20000 scans. 2D $^1$H-$^{13}$C HSQC NMR spectra were obtained using the Crisisgc2 HSQC program. The central solvent peak (DMSO) was used as an internal chemical shift reference point (δC/δH 39.5/2.49). The spectral widths were 5000 Hz and 20000 Hz for the $^1$H and$^{13}$C dimensions, respectively. Normally, the number of scans was 16 and 256 time increments were recorded in the $^{13}$C dimension.

Calculation of Potential Economic Impact on Lignocellulosic Biorefineries

It is assumed that the lignin content generated by one dry metric ton of corn stover is 18.5%. (30) Based on the experimental findings in this example, the aromatic aldehydes (vanillin and 4-hydroxybenzaldehyde) recovered from the pendant aromatic groups constitute approximately 6 wt % of the lignin content. Further, the ethanol production per dry metric ton of corn stover is reported to range from 47 to 76 gallons. (31) If one assumes that the average cost of the aromatic aldehydes is 12 US $/kg, (32) then the potential additional value created by these products per gallon of ethanol produced is estimated as follows.

Value added by aromatic aldehydes produced =

$$\frac{6 \text{ kg aldehydes}}{100 \text{ kg lignin}} \times \frac{185 \text{ kg lignin}}{1000 \text{ kg corn stover}} \times$$

$$\frac{1000 \text{ kg corn stover}}{76 \text{ gal ethanol}} \times \frac{12 \text{ US \$}}{1 \text{ kg aldehyde}} = \frac{1.75 \text{ US\$}}{\text{gal ethanol}}$$

If one assumes 47 gallons of ethanol produced per dry ton of corn Stover, the potential value added by the aromatic aldehydes produced is 2.83 U.S. $/gallon ethanol.

Results and Discussion

Figure 9:
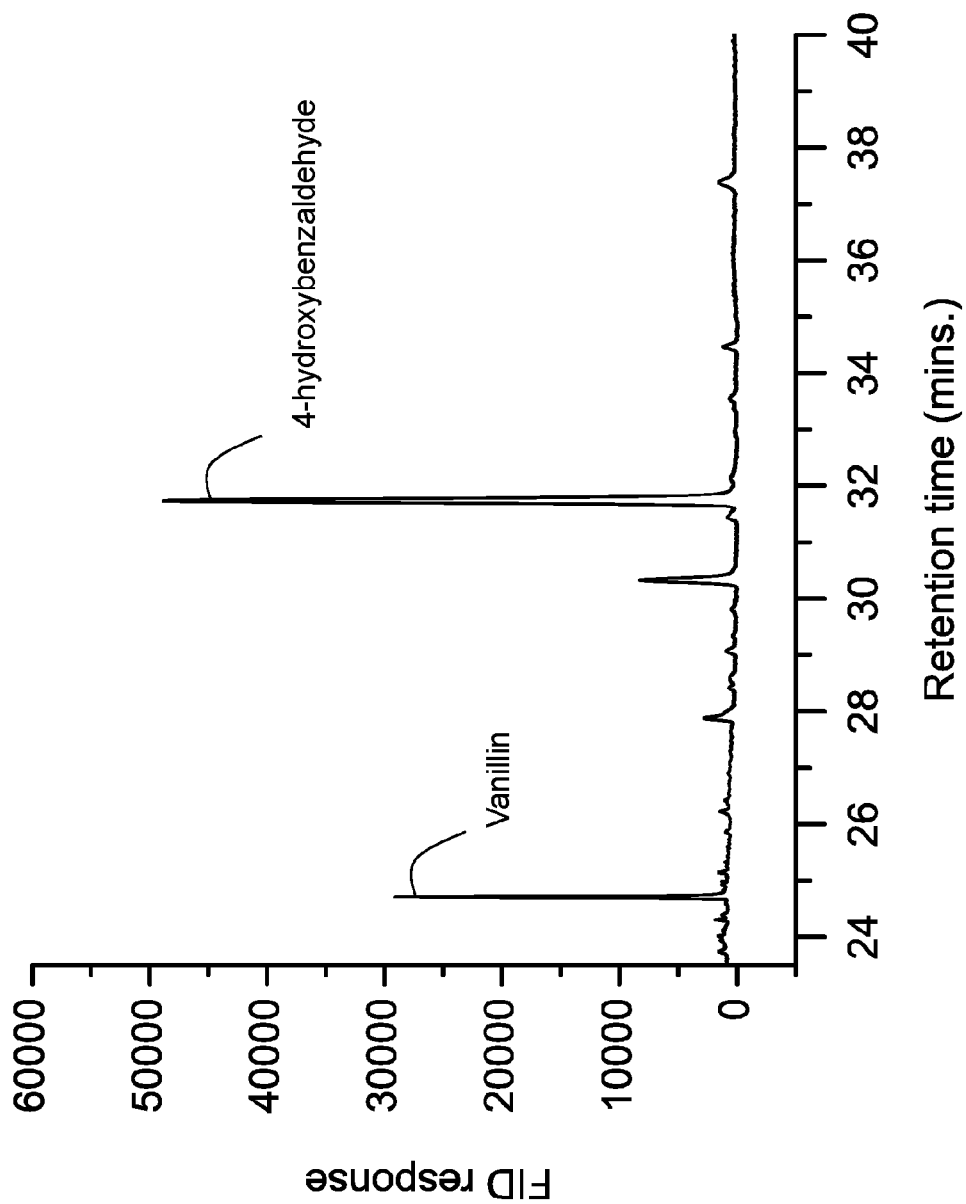
FIG. 9 shows a GC/FID spectrum for the products of the continuous ozonolysis of corn stover lignin in acetic acid (12 v/v % $H_2O$) at 70° C. Vanillin elutes at a retention time of 24.7 mins and 4-hydroxybenzaldehyde elutes at a retention time of 31.8 mins.
Figure 10C:
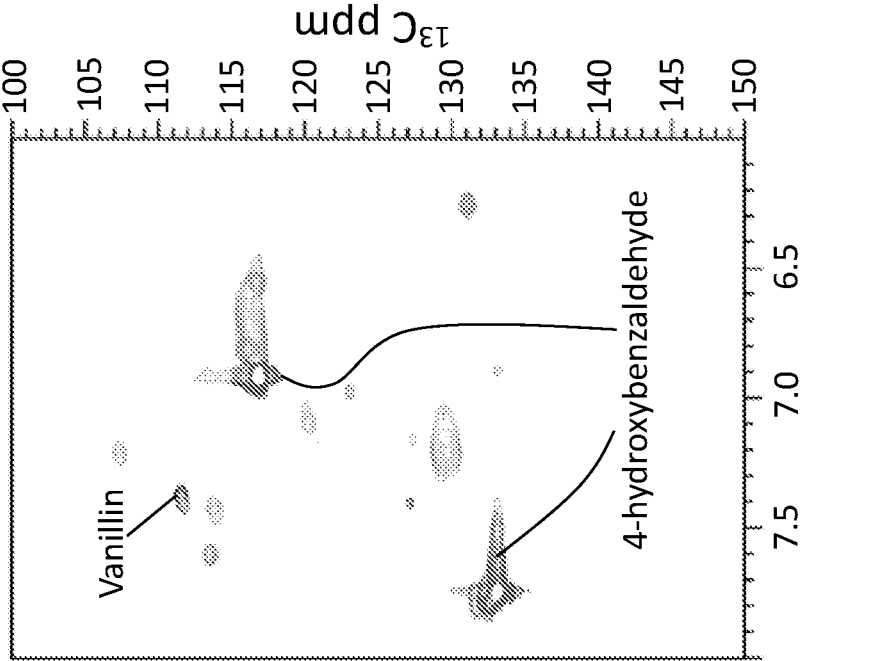
FIGS. 10A-10C shows 2D HSQC NMR spectra of corn stover lignin.
Figure 10B:
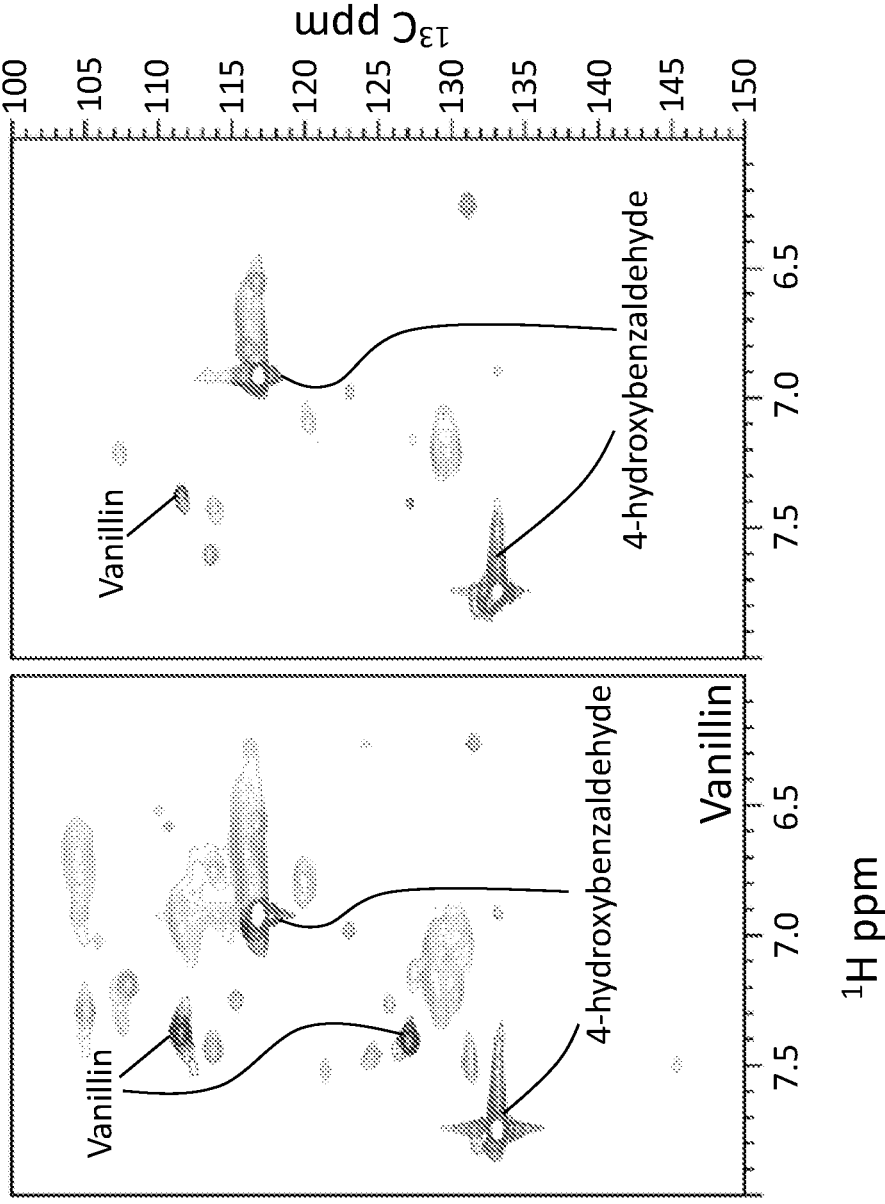
Figure 10A:
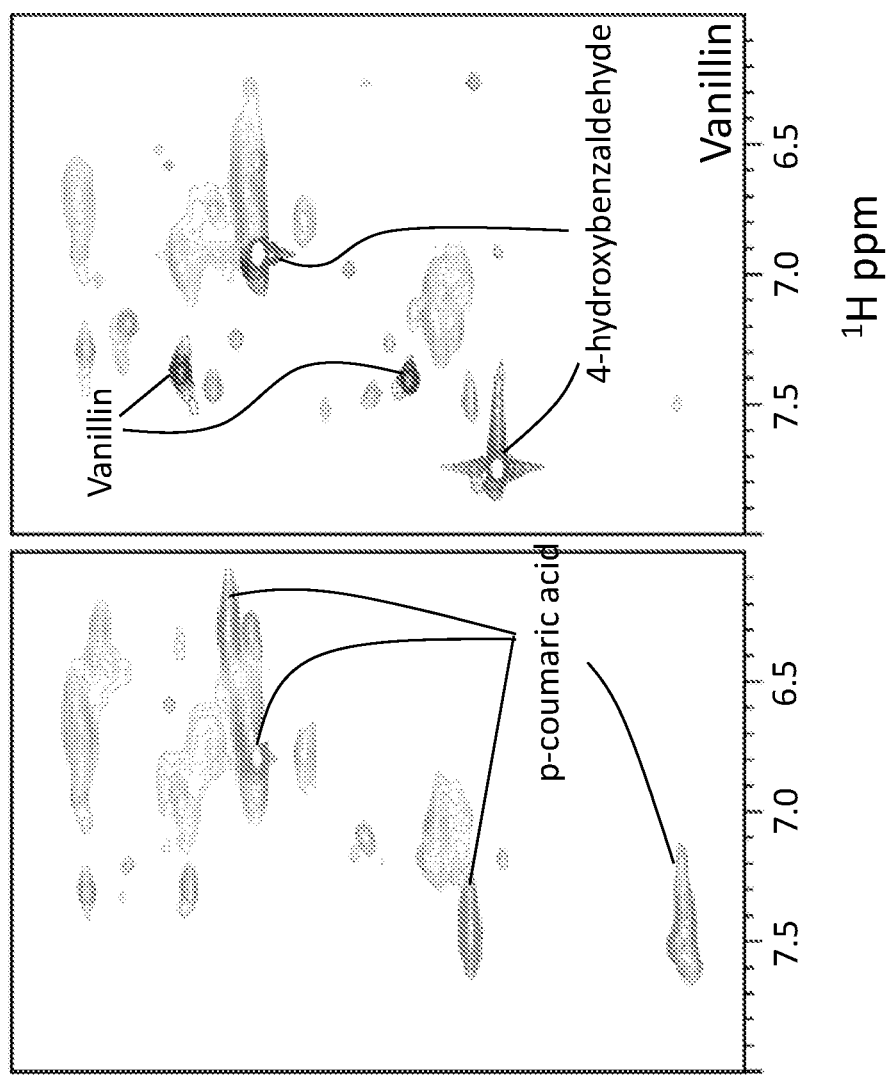

The ozonolysis of acetosolv lignin isolated from maize (Zea mays L.) in a continuous stirred tank reactor (CSTR) at 70° C. and ambient pressure yields 4-hydroxybenzaldehyde and vanillin along with minor quantities of the corresponding acids, 4-hydroxybenzoic acid and vanillic acid. Briefly, the lignin was dissolved in acetic or formic acid containing up to 20 v/v % water and pumped into the CSTR. A gaseous feed stream, containing approximately 3.5 wt % ozone in oxygen, was simultaneously sparged through the liquid phase at high flow rates such that the ozone was in significant excess relative to the lignin fed. The lignin solution was exposed to the ozone-laden gas stream for relatively short "contact times", defined as the ratio of the liquid holdup in the CSTR relative to the volumetric flow rate of the lignin solution. The contact time was typically on the order of a few minutes and may be varied by changing the feed rate of the liquid feed stream. As shown in FIG. 9, at a contact time of one minute, 4-hydroxybenzaldehyde and vanillin were produced almost exclusively at steady yields of up to 5.2 wt % and 1.5 wt %, respectively (based on the weight of dry lignin). Unexpectedly, the acid products (4-hydroxybenzoic acid and vanillic acid) were present in significantly lower yields of 0.62 and 0.18 wt %, respectively, rather than in stoichiometrically equivalent amounts relative to the aldehydic products. The total yield of these four products (ca. 7.5 wt % of the initial lignin) corresponds to virtually complete recovery of the aromatic portion of the pendant acid groups (i.e., the total yield is substantially the same as the amount of hydroxycinnamic groups on the lignin). As seen in Table 2, longer contact times lower the monomer yields presumably due to their oxidation upon extended exposure to ozone. Even though the products constitute only a small fraction of the initial lignin, the much higher values of the two major ones (vanillin and 4-hydroxybenzaldehyde) relative to cellulosic ethanol will contribute significantly to the overall profit generated by the biorefinery. Conservative projection suggests that the added value generated by these products per gallon of ethanol produced will be between 1.75-2.83 U.S. $ which is in the range of current gasoline price per gallon in the U.S. Further, the remaining lignin (~90% by weight) is still available for further valorization by other methods. (21)

distinctive resonances of the p-coumaric acid esters are lost upon ozonolysis. Prominent signals corresponding to the p-coumaric acid (PCA) (22, 23) observed at $\delta C/\delta H$ 145.0/7.51 (PCA a position), 130.5/7.48 (PCA 2,6), 115.5/6.70 (PCA 3,5) and 114.1/6.28 (PCA β) in the unreacted lignin agree well with literature values (FIG. 10A). Following ozone treatment at 70° C. with one minute contact time, the signals corresponding to the bound PCA (FIG. 10B) have much reduced intensity and are replaced by new resonances at $\delta C/\delta H$ 134.0/7.74, 117.1/6.91 and 128.7/9.75, characteristic of 4-hydroxybenzaldehyde and at $\delta C/\delta H$ 126.2/7.39, 114.6/6.91 and 110.7/7.35 for vanillin. These comparative NMR data conclusively show that the pendant aromatic groups are being completely converted to the oxoaromatic products (as evidenced by the total loss of the PCA signals and growth of the 4-hydroxybenzaldehyde/vanillin signals). The 4-hydroxybenzaldehyde and vanillin signals corresponding decay at the longer contact time of five minutes (FIG. 10C).

TABLE 2

Yields of aromatic monomers from continuous ozonolysis of corn stover lignin in a stirred reactor (T = 70° C.).
Yield of monomers (wt % of original lignin)

| Solvent | Contact time (mins.) | Vanillin[†] | 4-hydroxy-benzaldehyde[†] | Vanillic acid[‡] | 4-hydroxy-benzoic acid[‡] | Total aromatic monomers |
|---|---|---|---|---|---|---|
| Glacial Acetic Acid | 2.5 | 1.08 ± 0.07 | 2.85 ± 0.07 | 0.10 | 0.48 | 4.51 |
|  | 5.9 | 0.94 ± 0.06 | 2.6 ± 0.1 | 0.09 | 0.45 | 4.08 |
| Acetic Acid (12 v/v % water) | 1.0 | 1.5 ± 0.2 | 5.2 ± 0.4 | 0.18 | 0.62 | 7.50 |
|  | 2.5 | 1.39 ± 0.04 | 5.1 ± 0.3 | 0.20 | 0.82 | 7.29 |
|  | 5.0 | 1.2 ± 0.2 | 4.8 ± 0.2 | 0.17 | 0.60 | 6.77 |
|  | 10.0 | 0.60 ± 0.2 | 3.2 ± 0.5 |  |  |  |
| Acetic Acid (20 v/v % water) | 2.5 | 1.41 ± 0.03 | 4.2 ± 0.1 | 0.21 | 0.84 | 6.66 |
|  | 5.0 | 1.4 ± 0.1 | 4.52 ± 0.07 | 0.22 | 0.87 | 7.01 |
|  | 10.0 | 0.80 ± 0.02 | 3.3 ± 0.2 | 0.18 | 0.61 | 4.89 |
| Formic Acid (12 v/v %) | 1.0 | 0.58 ± 0.02 | 1.35 ± 0.08 | trace | 0.22 | 2.15 |
|  | 2.5 | 0.89 ± 0.02 | 4.4 ± 0.4 | 0.19 | 0.59 | 6.07 |
|  | 5.0 | 0.94 ± 0.02 | 4.2 ± 0.4 | 0.15 | 0.71 | 6.00 |
|  | 10.0 | 0.45 ± 0.02 | 4.15 ± 0.05 | 0.10 | 0.62 | 5.32 |

[†]Performed in at least triplicate, ± one standard deviation.
[‡]Measured in duplicate, estimated uncertainty ca. 20%.

Gel permeation chromatography (GPC) and NMR analyses confirm that the structure of the processed lignin is largely preserved at shorter contact times. Although GPC data (FIG. 6) suggest that there is no extensive depolymerization when increasing the contact time from one to five minutes, 2D HSQC NMR data indicate that there is severe loss of aromaticity. While the intensity of the aromatic resonances in the ozonized lignin does not change significantly from the original lignin at a contact time of one minute, the signals at 104.0/6.7, 111/6.96, 115.5/6.3 and 119/6.78 decrease at the longer contact time of five minutes. Additionally, the 2D HSQC NMR spectra of the products collected at the shorter contact time (one minute) show that while the ozonized lignin shares many of the structural features in the untreated lignin, some features are absent. The $^{13}C$ resonances for p-coumarate functionality of the lignin ester (Table 3) are in good agreement with literature values. (6) However, as revealed in FIGS. 10A-10C, some

TABLE 3

Measured $^{13}C$ NMR resonance values for lignin acylated with p-coumaric acid in the γ-position

| Carbon | $^{13}C$ resonance (ppm) |
|---|---|
| 1 | 126.0 |
| 2 | 130.4 |
| 3 | 116.1 |
| 4 | 159.9 |
| 5 | 116.1 |
| 6 | 130.4 |
| 7 | 144.9 |
| 8 | 114.2 |
| 9 | 166.7 |

Figure 11:
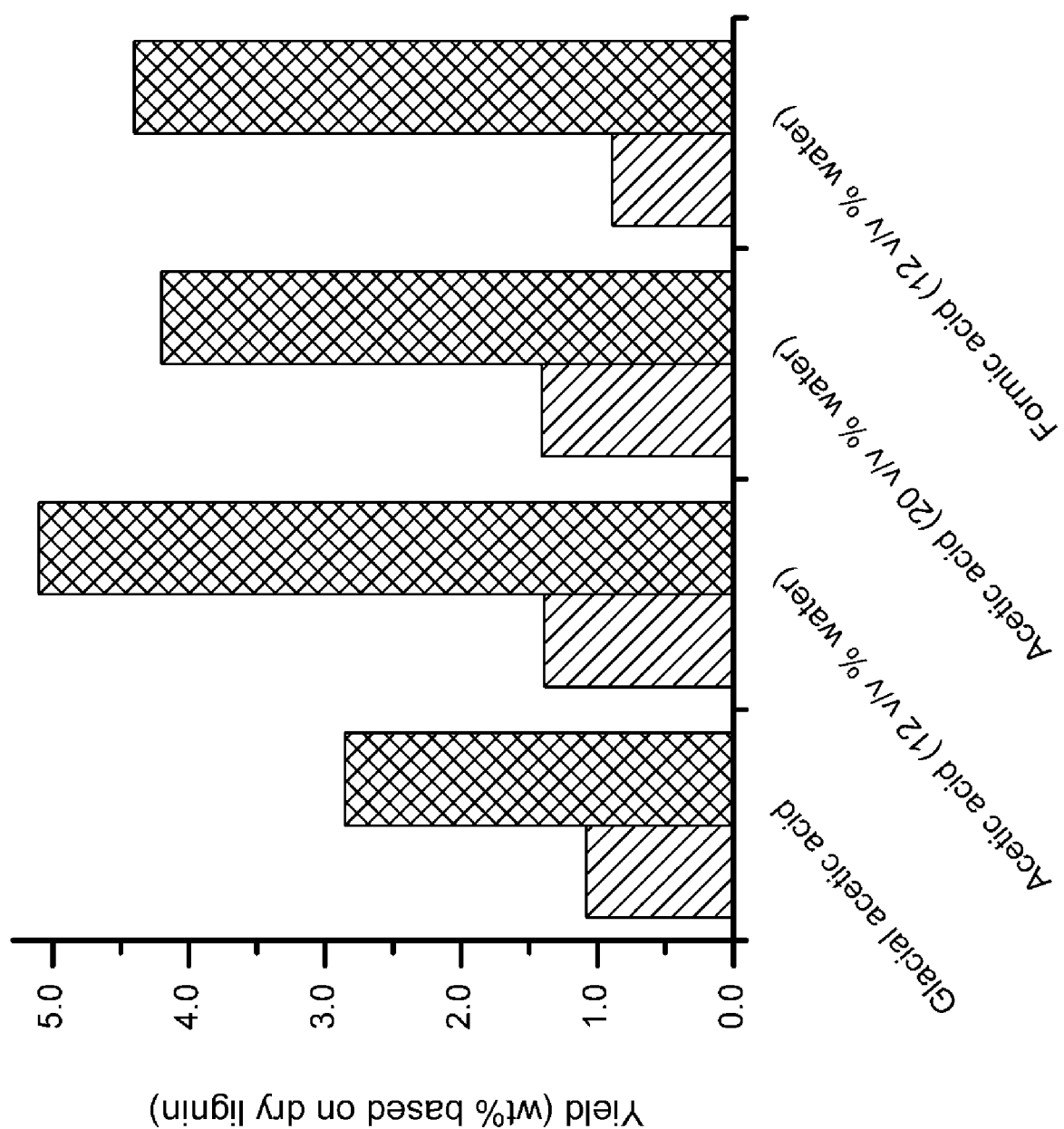
FIG. 11 shows the effect of solvent composition on the yields of vanillin (diagonal lines) and 4-hydroxybenzaldehyde (cross-hatch) during continuous ozonolysis of corn stover lignin with contact time of 2.5 mins and T=70° C.

An excess of the aldehyde products compared to the 50:50 ratio of acid (4-hydroxybenzoic acid and vanillic acid) to aldehydes (4-hydroxybenzaldehyde acid and vanillin) that would be expected from the decomposition of the secondary ozonide was observed (data not shown). According to the Criegee mechanism of olefin ozonolysis, (24) the initial intermediate is a primary ozonide (1,2,3-trioxolane) formed by the 1,3-dipolar cycloaddition of the $O_3$ molecule across the C=C double bond of the alkene. This cleaves to form an aldehyde or ketone fragment and a carbonyl oxide, also known as the Criegee intermediate. A further cycloaddition of the carbonyl oxide with a dipolarophile, usually the aldehyde or ketone resulting from the scission of the primary ozonide, yields a secondary ozonide (1,2,4-trioxolane). Secondary ozonides are relatively stable, decomposing only at elevated temperatures. However, they were not observed in either the NMR or infra-red spectra of the ozonolysis products. Further, the yields of monomer products at identical contact times (one minute) were essentially similar at 30 and 70° C. Clearly, this would not be the case if the observed products were formed by thermal decomposition of the secondary ozonide. One explanation could be the involvement of acetic acid as a participating solvent that interposes in the recombination of the carbonyl oxide and aldehyde fragment preventing the formation of the secondary ozonide. Acetic acid has been shown to be particularly efficient at trapping carbonyl oxide species. (25) However, no evidence exists to suggest a preference for the resulting acetoxyhydroperoxide to form at the lignin end of the olefin rather than at the aromatic moiety, a necessary condition to account for the observed excess of the aromatic aldehyde. Higher yields of the two aromatic aldehydes were observed when small quantities of water were added to the solvent (FIG. 11). Direct production of aldehydes via ozonolysis by using an organic solvent containing low concentrations of dissolved water has been previously reported. (26, 27) For the ozonolysis of anethole to anisaldehyde in a solution of ethyl acetate with 10 wt % water, (28) the mechanism was shown to involve the addition of water to the carbonyl oxide to yield a gem-hydroperoxy alcohol which decomposes to form hydrogen peroxide and the aldehyde in 99.5% purity.

The ozonolysis treatment was applied to two additional lignins, one extracted from wheat straw (a grass lignin) and the other from American white oak (a woody lignin), using an ethyl acetate organosolv process. Wheat straw lignin is reported have similar acylation as maize lignin, but with lower abundance. (7) The yields of vanillin (1.29 wt %) and 4-hydroxybenzaldehyde (1.77 wt %), confirm the decreased presence of the hydroxycinnamic acids. Lignins derived from hardwoods are partially acetylated in the γ-position of the alkyl side chain and consequently have no peripheral olefin bound aromatic groups that would yield aromatic monomers after ozone treatment. Indeed, no 4-hydroxybenzaldehyde was observed from ozonolysis of the white oak lignin and the yield of vanillin was approximately a third of that observed with maize lignin.

To determine if the aromatic monomer products were indeed derived from the hydroxycinnamic acids bound to the lignin polymer rather than from depolymerization of the lignin backbone, the ozone-treated lignin was separated and ozonized again. The products from an initial ozonolysis reaction, with a contact time of 2.5 minutes in acetic acid (12 v/v % water), were extracted with diethyl ether to remove the aromatic monomers. The residual polymeric material was dried and re-dissolved in a fresh solution of acetic acid. It was re-ozonized in the CSTR with a contact time of 2.5 minutes. Yields of vanillin and 4-hydroxybenzaldehyde were significantly lower (<0.05 wt %) than with the virgin lignin, confirming that the predominant source of the aromatic monomers are the pendant p-coumarates and ferulates rather than the lignin backbone.

Continuous ozonolysis of grass lignins in either aqueous acetic or formic acid thus offers a simple method for improving the economics of lignocellulosic biorefineries, using reagents that are generally regarded as safe.

REFERENCES FOR EXAMPLE 2

1 C. O. Tuck, E. Pérez, I. T. Horvath, R. A. Sheldon, M. Poliakoff, Valorization of biomass: deriving more value from waste. *Science* 337, 695-699 (2012).
2 R. Vanholme, B. Demedts, K. Morreel, J. Ralph, W. Boerjan, Lignin biosynthesis and structure. *Plant Physiology* 153, 895-905 (2010).
3 M. Li, Y. Pu, A. J. Ragauskas, Current understanding of the correlation of lignin structure with biomass recalcitrance. *Frontiers in Chemistry* 4, 45 (2016).
4 A. J. Ragauskas et al., Lignin valorization: improving lignin processing in the biorefinery. *Science* 344, 1246843 (2014).
5 M. Graglia, N. Kanna, D. Esposito, Lignin refinery: towards the preparation of renewable aromatic building blocks. *ChemBioEng Reviews* 2, 377-392 (2015).
6 J. Ralph et al., Pathway of p-coumaric acid incorporation into maize lignin as revealed by NMR. *Journal of the American Chemical Society* 116, 9448-9456 (1994).
7 R. Sun, X. F. Sun, S. Q. Wang, W. Zhu, X. Y. Wang, Ester and ether linkages between hydroxycinnamic acids and lignins from wheat, rice, rye, and barley straws, maize stems, and fast-growing poplar wood. *Industrial Crops and Products* 15, 179-188 (2002).
8 C. Doree, M. Cunningham, LXXVI. The action of ozone on cellulose. Part III. Action on beech wood (lignocellulose). *Journal of the Chemical Society, Transactions* 103, 677-686 (1913).
9 K. V. Sarkanen, A. Islam, C. D. Anderson, "Ozonation" in *Methods in Lignin Chemistry*, S. Y. Lin, C. W. Dence Eds. (Springer, Berlin, 1992). Springer Series in Wood Science, Chap. 26, pp. 387-406.
10 T. Akiyama, et al., Erythro/threo ratio of β-O-4 structures as an important structural characteristic of lignin. Part 4: Variation in the erythro/threo ratio in softwood and hardwood lignins and its relation to syringyl/guaiacyl ratio. *Holzforschung* 59, 276-281 (2005).
11 J. Quesada, M. Rubio, D. Gómez, Ozonation products of organosolvolytic extracts from vegetal materials. *Journal of Agricultural and Food Chemistry* 46, 692-697 (1998).
12 A. Rahimi, A. Ulbrich, J. J. Coon, S. S. Stahl, Formic-acid-induced depolymerization of oxidized lignin to aromatics. *Nature* 515, 249-252 (2014).
13 L. Shuai, et al., Formaldehyde stabilization facilitates lignin monomer production during biomass depolymerization *Science* 354, 329-333 (2016).
14 J. C. Del Rio, G. Marques, J. Rencoret, A. T. Martinez, A. Gutierrez, Occurrence of naturally acetylated lignin units. *Journal of Agricultural and Food Chemistry* 55, 5461-5468 (2007).
15 F. Lu, et al., Naturally p-hydroxybenzoylated lignins in palms. *BioEnergy Research* 8, 934-952 (2015).
16 F. Lu, J. Ralph, Preliminary evidence for sinapyl acetate as a lignin monomer in kenaf. *Chemical Communications* 90-91, (2002).
17 S. Withers, et al., Identification of grass-specific enzyme that acylates monolignols with p-coumarate. *Journal of Biological Chemistry* 287, 8347-8355 (2012).

18 F. Lu, J. Ralph, Detection and determination of p-coumaroylated units in lignins. *Journal of Agricultural and Food Chemistry* 47, 1988-1992 (1999).
19 J. H. Grabber, S. Quideau, J. Ralph, p-Coumaroylated syringyl units in maize lignin: Implications for β-ether cleavage by thioacidolysis. *Phytochemistry* 43, 1189-1194 (1996).
20 R. M. Dorland, H. Hibbert, H. Formic acid as a solvent for ozonization investigations. *Can. J. Res., Sect. B* 18B, 30-34 (1940).
21 C. Li, X. Zhao. A. Wang, G. W. Huber, T. Zhang, Catalytic transformation of lignin for the production of chemicals and fuels. *Chemical Reviews* 115 11559-11624 (2015).
22 J. C. del Rio, et al., Structural characterization of wheat straw lignin as revealed by analytical pyrolysis, 2D-nmr, and reductive cleavage methods. *Journal of Agricultural and Food Chemistry* 60, 5922-5935 (2012).
23 T. You, L. Zhang, S. Guo, L. Shao, F. Xu, F. Unraveling the structural modifications in lignin of Arundo donax Linn. during acid-enhanced ionic liquid pretreatment. *Journal of Agricultural and Food Chemistry* 63, 10747-10756 (2015).
24 R. Criegee, Mechanism of ozonolysis. Angewandte Chemie International Edition in English 14, 745-752 (1975).
25 H. Hanaki, Y. Fukatsu, M. Harada, Y. Sawaki, Cyclic mechanism in the trapping of carbonyl oxides with alcohols and carboxylic acids. *Tetrahedron Letters* 45, 2559-2561 (2004)
26 C. E. Schiaffo, P. H. Dussault, Ozonolysis in solvent/water mixtures: direct conversion of alkenes to aldehydes and ketones. *Journal of Organic Chemistry* 73, 4688-4690 (2008).
27 P. Hannen, H. Haeger, M. Roos, Synthesis of omega-amino carboxylic acids and their esters from unsaturated fatty acid derivatives. WO2011160730A1 (2011).
28 J. Yu, M. Shen, L. Deng, L. Gan, C. Ha, Facile one-pot synthesis of anisaldehyde. *Chemistry of Natural Compounds* 48, 541-543 (2012).
29 I. Cybulska, G. Brudecki, K. Rosentrater, J. L. Julson, H. Lei, Comparative study of organosolv lignin extracted from prairie cordgrass, switchgrass and corn stover. *Bioresource Technology* 118, 30-36 (2012).
30 J. D. Stephen, W. E. Mabee, J. N. Saddler, Will second-generation ethanol be able to compete with first-generation ethanol? Opportunities for cost reduction. *Biofuels. Bioprod. Bioref* 6, 159-176 (2012).
31 F. K. Kazi, et al., Techno-economic comparison of process technologies for biochemical ethanol production from corn stover. *Fuel* 89, S20-S28 (2010).
32 N. Smolarski, High-value opportunities for lignin: unlocking its potential. Frost & Sullivan, http://www.greenmaterials.fr/wp-content/uploads/2013/01/High-value-Opportunities-for-Lignin-Unlocking-its-Potential-Market-Insights.pdf. (2012) Accessed 20 Mar. 2017.

Example 3

Methods

A 1 wt % solution of lignin dissolved in 88 v/v % acetic acid/water was ozonized at 70° C. using the previously described continuous method (Examples 1 and 2) with a residence time of 2.5 minutes. 100 mL of the product stream were collected and placed in a 500 mL ISCO pump. This product stream was filtered by passing it through a 47 mm diameter DuraMem™ membrane with a 300 Da molecular weight cutoff. The membrane was fitted in a Millipore High Pressure Filter Holder and the filter disk was presoaked in acetic acid for ca. 10 hours prior to use. The ISCO pump was used to pump the ozonized lignin solution through the membrane at a pressure of approximately 25 bar. The filtrate was collected in 10 mL batches and the fourth batch collected was used for analysis. The filtrate was analyzed by Gas Chromatography with Flame Ionization Detector (GC FID) and by Gel Permeation Chromatography (GPC).

Results

Figure 12:
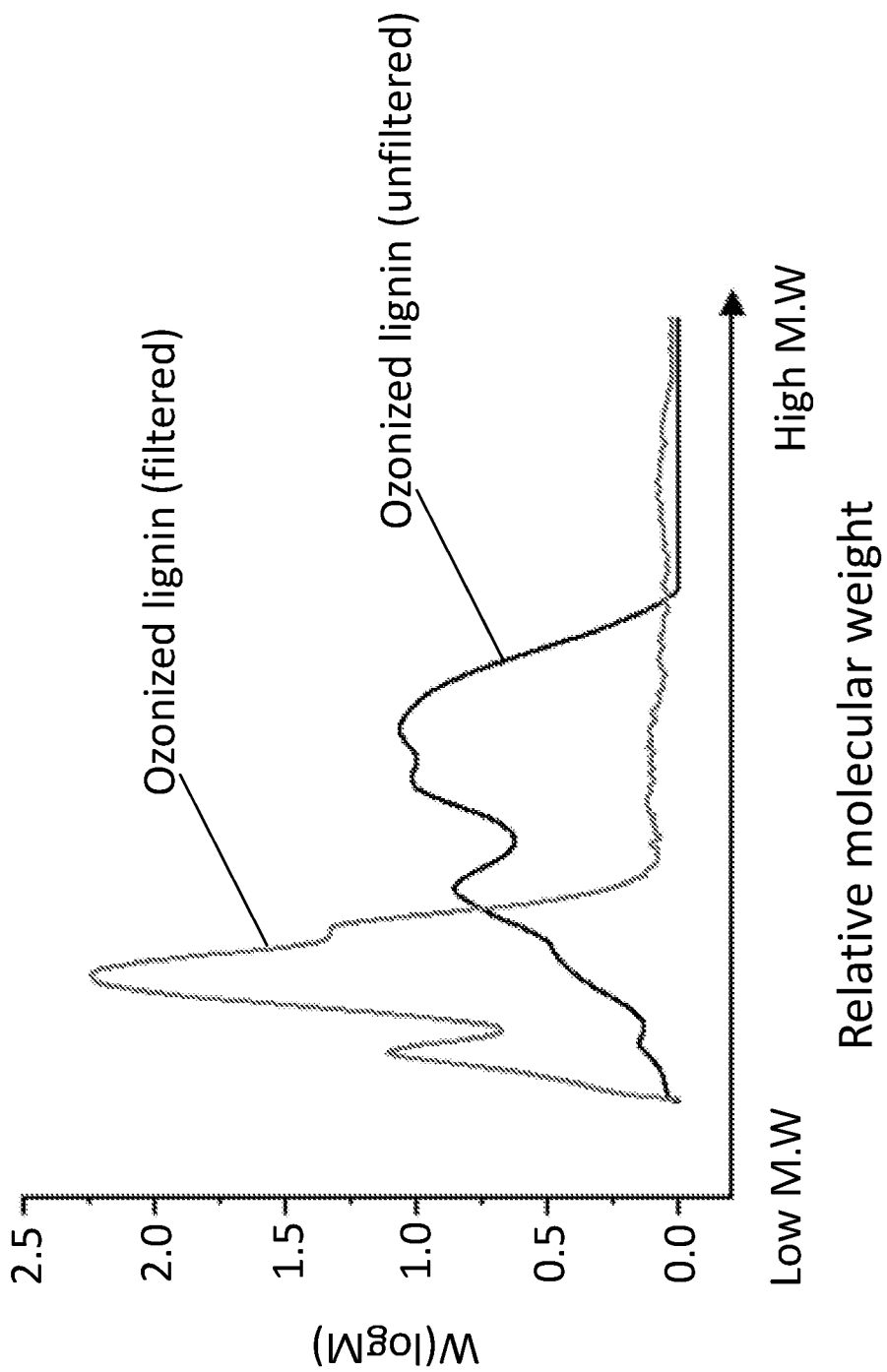
FIG. 12 shows GPC data comparing the relative molecular weight distributions of ozonized lignin in acetic acid solution (unfiltered) and the filtrate of the ozonized lignin solution after passing through a DuraMem™ 300 Da. membrane.
Figure 13:
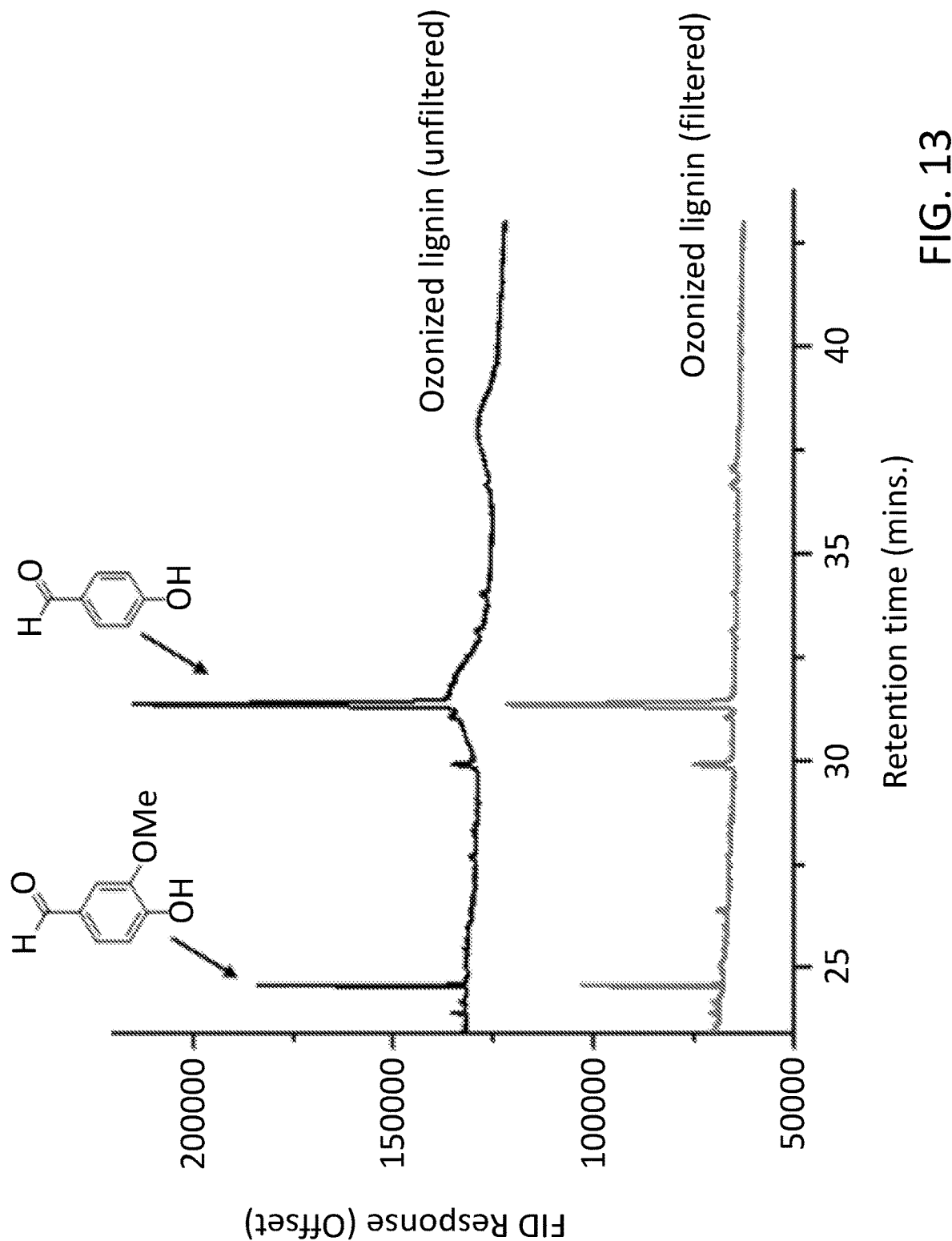
FIG. 13 shows GC FID spectra of ozonized lignin in acetic acid solution (unfiltered; offset by +60000) and the filtrate of the ozonized lignin solution after passing through a DuraMem™ 300 Da. membrane. Note that high molecular weight compounds in the product mixture that appear at higher GC retention times (38-40 mins) are absent in the red GC FID spectra corresponding to the filtrate.

The physical appearance of the filtrate differed as compared to the ozonized lignin. The color of the filtrate is much lighter compared to the product stream being filtered indicating substantial retention of the chromophore rich polymeric lignin material by the filter. The GPC spectra (FIG. 12) of the filtrate clearly show that the high molecular weight polymeric material present in the ozonized lignin is absent from the filtrate and only the low molecular weight products have passed through the membrane. This is confirmed by the GC FID data (FIG. 13) which show high concentrations of vanillin and 4-hydroxybenzaldehyde in both the ozonized lignin and the filtrate. Quantification of the GC FID data indicates that 72% of the vanillin and 78% of the 4-hydroxybenzaldehyde pass through the membrane. However, these numbers are for a single pass sample and it is anticipated that higher yields could be obtained by washing the retentate with fresh solvent.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method for processing lignin, the method comprising:
    flowing a lignin composition comprising a lignin polymer and a solvent through a reaction chamber of a continuous flow reactor, the lignin polymer comprising hydroxycinnamic groups bound to a polymeric backbone;
    flowing ozone through the reaction chamber containing the lignin composition under conditions to maximize oxidative cleavage of the hydroxycinnamic groups to produce one or more types of aromatic monomers while minimizing oxidative cleavage of the polymeric backbone; and
    collecting the one or more types of aromatic monomers.
2. The method of claim 1, wherein the lignin is extracted from herbaceous biomass.
3. The method of claim 2, wherein the herbaceous biomass is corn stover.

4. The method of claim 1, wherein the method is carried out at a flow rate of the lignin composition and a holdup volume selected to provide a reaction time of less than 10 minutes.

5. The method of claim 1, wherein the solvent comprises a short chain carboxylic acid.

6. The method of claim 5, wherein the short chain carboxylic acid is selected from acetic acid, formic acid, propionic acid, and combinations thereof.

7. The method of claim 5, wherein the solvent further comprises water.

8. The method of claim 7, wherein the amount of water is less than 20% by volume.

9. The method of claim 1, wherein the method is carried out at a reaction temperature in the range of from 20° C. to 80° C.

10. The method of claim 1, wherein the method is carried out at a flow rate of the lignin composition and a holdup volume selected to provide a reaction time of less than 5 minutes; the solvent is a short chain carboxylic acid or the short chain carboxylic acid combined with water; the method is carried out at a reaction temperature in the range of from 20° C. to 80° C.; and the lignin is extracted from herbaceous biomass.

11. The method of claim 10, wherein the solvent is acetic acid or acetic acid combined with water.

12. The method of claim 1, wherein the total yield of the one or more types of aromatic monomers, as measured by weight percent of the weight of the lignin in the lignin composition, is substantially the same as the amount of hydroxycinnamic groups on the lignin polymer, as measured by weight percent of the weight of the lignin in the lignin composition.

13. The method of claim 1, wherein the conditions result in substantially no oxidative cleavage of the polymeric backbone.

14. The method of claim 1, wherein the total yield of the one or more types of aromatic monomers is at least 7% by weight as compared to the weight of the lignin in the lignin composition.

15. The method of claim 14, wherein the one or more types of aromatic monomers are selected from vanillin, 4-hydroxybenzaldehyde, vanillic acid, 4-hydroxybenzoic acid, and combinations thereof.

16. The method of claim 14, wherein the conditions result in substantially no oxidative cleavage of the polymeric backbone.

17. The method of claim 16, wherein the one or more types of aromatic monomers are selected from vanillin, 4-hydroxybenzaldehyde, vanillic acid, 4-hydroxybenzoic acid, and combinations thereof.

18. The method of claim 1, further comprising separating the one or more types of aromatic monomers from the polymeric backbone by size-selective membrane filtration.

19. The method of claim 18, wherein more than 95% of the polymeric backbone is retained by a membrane of the size-selective membrane filtration while selectively rejecting the one or more types of aromatic monomers.

20. The method of claim 18, further comprising subjecting the separated polymeric backbone to an additional depolymerization process to depolymerize the polymeric backbone.

* * * * *

UNITED STATES PATENT AND TRADEMARK OFFICE
CERTIFICATE OF CORRECTION

PATENT NO. : 10,745,335 B2
APPLICATION NO. : 16/317173
DATED : August 18, 2020
INVENTOR(S) : Bala Subramaniam et al.

It is certified that error appears in the above-identified patent and that said Letters Patent is hereby corrected as shown below:

In the Specification

Column 14, Lines 11-12:
Delete the phrase "Bruker AVUI 500 MHz spectrometer." and replace with --Bruker AVIII 500 MHz spectrometer.--.

Column 16, Line 4:
Delete the phrase "(PCA a position)," and replace with --(PCA α position),--.

Signed and Sealed this
Third Day of November, 2020

Andrei Iancu
*Director of the United States Patent and Trademark Office*